US006809113B2

(12) United States Patent
Laborde et al.

(10) Patent No.: US 6,809,113 B2
(45) Date of Patent: Oct. 26, 2004

(54) ANTAGONISTS OF MCP-1 FUNCTION AND METHODS OF USE THEREOF

(75) Inventors: Edgardo Laborde, Foster City, CA (US); Louise Robinson, San Carlos, CA (US); Fanying Meng, San Francisco, CA (US); Brian T. Peterson, San Francisco, CA (US); Hugo O. Villar, La Jolla, CA (US); Steven E. Anuskiewicz, San Bruno, CA (US); Yoshiro Ishiwata, Aichi-gun (JP); Shoji Yokochi, Inabe-gun (JP); Yukiharu Matsumoto, Gifu (JP); Takuji Kakigami, Inabe-gun (JP); Hideaki Inagaki, Anjoh (JP); Takahito Jomori, Nagoya (JP); Kouji Matsushima, Matsudo (JP)

(73) Assignees: Telik, Inc., Palo Alto, CA (US); Sanwa Kagaku Kenkyusho Co., Nagoya (JP)

( * ) Notice: Subject to any disclaimer, the term of this patent is extended or adjusted under 35 U.S.C. 154(b) by 179 days.

(21) Appl. No.: 10/087,208

(22) Filed: Feb. 27, 2002

(65) Prior Publication Data

US 2003/0105085 A1 Jun. 5, 2003

Related U.S. Application Data

(60) Provisional application No. 60/272,792, filed on Mar. 1, 2001.

(51) Int. Cl.$^7$ .................... A61K 31/35; A61K 31/41; A61K 31/44
(52) U.S. Cl. .................... 514/456; 514/256; 514/337; 514/356; 514/363; 549/60; 549/366; 548/136; 548/146; 548/204; 548/253; 548/254; 546/282.7; 544/333; 544/335
(58) Field of Search ................ 549/60, 366; 544/333, 544/335; 546/282.7; 548/136, 146, 204, 253, 254; 514/256, 337, 356, 363, 456

(56) References Cited

U.S. PATENT DOCUMENTS

| | | | |
|---|---|---|---|
| 3,823,144 A | 7/1974 | Schmitt et al. | 260/268 |
| 4,269,990 A | 5/1981 | May et al. | 548/315 |
| 5,977,108 A | 11/1999 | Kikuchi et al. | 514/249 |
| 6,140,338 A | 10/2000 | Naya et al. | 514/299 |
| 6,288,103 B1 | 9/2001 | Faull et al. | 514/419 |
| 6,316,449 B1 | 11/2001 | Bratton et al. | 514/252.04 |
| 6,329,402 B1 | 12/2001 | Kikuchi et al. | 514/341 |
| 6,342,516 B1 | 1/2002 | Umeda et al. | 514/397 |

FOREIGN PATENT DOCUMENTS

| | | |
|---|---|---|
| EP | 0 004 187 A1 | 9/1979 |
| EP | 0 234 098 A1 | 9/1987 |
| FR | 2 001 284 A | 9/1969 |
| GB | 1 250 611 | 10/1974 |
| JP | 2-144546 | 6/1990 |
| JP | 9-255572 | 9/1997 |
| WO | 92/14710 | 9/1992 |
| WO | 97/24325 | 7/1997 |
| WO | 97/44329 | 11/1997 |
| WO | 98/02151 | 1/1998 |
| WO | 98/06703 | 2/1998 |
| WO | 98/27815 | 7/1998 |
| WO | 98/04554 | 5/1999 |
| WO | 99/40072 | 8/1999 |
| WO | 01/57003 | 8/2001 |
| WO | 01/57021 | 8/2001 |
| WO | 01/57044 | 8/2001 |

OTHER PUBLICATIONS

Alcami et al., "Blockade of Chemokine Activity by a Soluble Chemokine Binding Protein form Vaccinia Virus", *J Immunol*, 160:624–633 (1998).
Antoniades et al., "Expression of monocyte chemoattractant protein 1 mRNA in human idiopathic pulmonary fibrosis", *Proc Natl Acad Sci USA*, 89:5371–5375 (1992).
Ajuebor et al., "Endogenous monocyte chemoatttractant protein–1 recruits monocytes in the zymosan peritonitis model", *Journal of Leukocyte Biology*, vol. 63:108–116, Jan. 1998.
Baggiolini et al., "Human Chemokines; an update", Annu rev Immunol (1997), pp. 15:675–705.
Baggiolini et al., Chemokines and Leukocyte Traffic, Nature vol.: 392:9 pp. 565–568, (1998).
Boring et al., "Decreased lesion formation in CCR2$^{-/-}$mice reveals a role for chemokines in the initiation of atherosclerosis", *Nature*, 394:894–897 (1998).
Bright et al., "Identification of a Non Peptidic Rantes Antagonist", *Bioorg Med Chem Lett*, 8:771–774 (1998).
Campbell et al., "Monocyte Chemoattractant Protein–1 Mediates Cockroach Allergen–Induced Bronchial Hyperreactivity in Normal but Not CCR2$^{-/-}$Mice: The Role of Mast Cells", *J Immunol*, 163:2160–2167 (1999).
Luster, "Chemokines__Chemotactic Cytokines That Mediate Inflammation", *The New England Journal of Medicine*, pp. 436–445, Feb. 12, 1998.
Folkman and Shing, "Control of Angiogensis by Heparin and Other Sulfated Polysaccharides", *Adv Exp Med Biol.*, 313:355–364 (1992).
Forbes et al., "CCR2B Receptor Antagonist: Conversion of a Weak HTS Hit to a Potent Lead Compound", *Bioorg Med Chem. Lett*, 10:1803–1806 (2000).

(List continued on next page.)

*Primary Examiner*—Amelia A. Owens
(74) *Attorney, Agent, or Firm*—Cooley Godward LLP

(57) ABSTRACT

Compounds which are antagonists of MCP-1 function and are useful in the prevention or treatment of chronic or acute inflammatory or autoimmune diseases, especially those associated with aberrant lymphocyte or monocyte accumulation such as arthritis, asthma, atherosclerosis, diabetic nephropathy, inflammatory bowel disease, Crohn's disease, multiple sclerosis, nephritis, pancreatitis, pulmonary fibrosis, psoriasis, restenosis, and transplant rejection; pharmaceutical compositions comprising these compounds; and the use of these compounds and compositions in the prevention or treatment of such diseases.

40 Claims, No Drawings

OTHER PUBLICATIONS

36Gosling et al., "MCP–1 deficiency reduces susceptibility to atherosclerosis in mice that over express human apo37lipoprotein B", *J Clin Invest,* 103:773–778 (1999).

Gu et al., "Absence of Monocyte Chemoattractant Protein–1 Reduces Atherosclerosis in Low Density Lipoprotein Receptor–Deficient Mice", *Mol Cell,* 2:275–281 (1998).

Hesselgesser, "Identification and Characterization of Small Molecule Functional Antagonists of the CCR1 Chemokine Receptor", *J. Biol Chem,* 273:15687–15692 (1998).

Hoogewerf et al., "Glycosaminoglycans Mediate Cell Surface Oligomerization of Chemokines", *Biochemistry* 36:13570–13578, (1997).

Hosaka et al., "Expression of the Chemokine Superfamily in Rheumatoid Arthritis", *Clin Exp Immunol,* 97:451–457. (1994).

Hsieh et al., "Immunotherapy Suppresses the Production of monocyte chemotactic and activating factor and augments the production of IL–8 in Children with Asthma", *J Allergy Clin Immunol,* 98:580–587 (1996).

Kitano M. et al., "Synthesis and Biological Activity of N–(Aminoiminomethyl)–1H–Idoleca Rboxamide Inhibitors", Chem and Pharm Bulletin, Pharmaceutical Society of Japan, vol. 47, No. 11, Nov. 1999, pp. 1538.

Koch et al., "Enhanced Production of Monocyte Chemoattractant Protein–1 in Rheumatoid Arthritis", *J Clin Invest,* 90:772–779, (1992).

Alam et al., "Increased MCP–1, RANTES, and MIP–1$\alpha$in Bronchoalveolar Lavage Fluid of Allergic Asthmatic Patients", *Am J Respir Crit Care Med,* 153:1398–1404. (1996).

Kunkel et al., "The Role of Chemokines in Inflammatory Joint Disease", *J Leukocyte Biol,* 59:6–12 (1996).

Kurashima et al., "Increase of Chemokine Levels in Sputum Precedes Exacerbation of Acute Asthma Attacks", *J Leukocyte Biol,* 59:313–316, ((1996).

Kuschert et al., "Glycosamineoglycans interact selectively with chemokines and moldulate receptor binding and cellular responses", *Biochemistry* 38:12959–12968, (1999).

Liang et al., "Identification and characterization of a potent, selective and orally active antagonist of the cc chemokine receptor–1", *The Journal of Biological Chemistry,* vol. 25:19000–19008, Jun. 23, 2000.

McFadden and Kelvin, "New Strategies for Chemokine Inhibition and Modulation", *Biochem Pharmacol,* 54:1271–1280 (1997).

Mirzadegan et al., "Identification of the binding site for a novel class of CCR2bcemokine receptor antagonists. . . ", The American Society for Biochemistry and Molecular Biology, Inc., manuscript M000692200, (2000).

Moore et al., "Tumor angiogenesis is regulated by CXC chemokines", *J Lab Clin Med,* 132:97–103 (1998.

Moore et al., "CXC Chemokine Modulation of angiogenesis . . . ", J Invesitgative Medicine, vol. 46:113–120 (1998).

Murphy,:The Molecular Biology of Leukocyte Chemoattractant Receptors, *Annu Rev Immun,* 12:593–633, (1994).

Nelken et al., "Monocyte Chemoattractant Protein–1 in Human Atheromatous Plaques", *J. Clin Invest,* 88:1121–1127 (1991).

Okada et al., "Synthesis and Antitumor Activities of Water–Soluble Benzoylphenylureas", *Chem Pharm Bull,* 47:430–433, (1999).

Okada et al., "Synthesis and Antitumor Activities of Prodrugs of Benzoylphenylureas", *Chem Pharm Bull* 42:57–61, (1994).

Okada et al., "Synthesis and Antitumor Activities of Novel Benzoylphenylurea Derivatives", *Chem Pharm Bull,* 39:2308–2315 (1991).

Proost et al., "The Role of Chemokines in Inflammation", *Int J Clin Lab Res,* 26:211–233, (1996).

Robinson et al., "Chemokine expression in Rheumatoid Arthritis . . . ", *Clin Exp Innumol* 101:398–407 (1995).

Rollins, "Chemokines", *Blood,* vol. 90, No. 3, pp. 909–928, Aug. 1, 1997.

Rousseau, Jean–Francois et al., Chemical Abstract, "Regioselective ortho–directed metalation and electrophilic substitution of indoleand indoling –5–(N–phenyl) carboxamides" retrieved from STN database accession No. 136:355126 XP002206081 abstract & Heterocycles 92001), 55(12), 2289–2304.

Rovin et al., "Chemotactic Factors and Renal Inflammation", *American Journal of Kidney Diseases,* 31:1065–1084, Jun. 1998.

Wellstein and Czubayko, "Inhibition of fibroblast growth factors", *Breast Cancer Res Treat,* 38:109–119 (1996).

White, "Identification of a Potent, Selective Non–peptide CXCR2 Antagonist That Inhibits Interleukin–8–induced Neutrophil Migration", *J. Bio Chem,* 273:10095–10098 (1998).

Wrenshall et al., "Modulation of macrophage and B cell function by glycosaminoglycans", Journal of Leukocyte Biology, vol. 66:391–400, Sep. 1999.

Yang et al., "Fully human anti–interleukin–8 monoclonal antibodies: potential therapeutics for the treatment of inflammatory disease states", Jounal of Leukocyte Biology, vol. 66: 401–410, Sep. 1999.

Yla–Hertuala et al., "Expression of Monocyte Chemoattractant Protein 1 in Macrophage–Rich Areas of Human and Rabbit Ateroslerotic Lesions", *Proc Natl Acad Sci USA,* 88:5252–5256 (1991).

Zetzsche et al., Crossfire Beilstein 'Online' Beilstein Institut Aur Forerderung Der Wissenschaten, Frankfurt, DE; Abstract, Chemische Berichte, vol. 72, 1939, p. 1599.

Rovin, "Chemokines as Therapeutic Targets in Renal Inflammation", American Journal of Kidney Diseases, 34:761–767, Oct. 1999.

Rovin, "Chemokine blokade as a therapy for renal disease", *Current Opinion in Nephrology and Hypertension,* 13:225–232, (2000).

Rovin et al., "A Novel Polymorphism in the MCP–1 Gene Regulatory Region That influences MCP–1 Expression", *Biochemical and Biophysical Research Communications,* 259, pp. 344–348, (1999).

Saunders and Tarby, "Opportunities for novel therapeutic agents acting at chemokine receptors", Drug Discovery Today, vol. 4 No. 2 (1999).

Schall, "Biology of the RANTES/SIS Cytokine Family", *Cytokine,* 3:165–183, (1991).

Sendo et al., "Regulation of leukocyte adherence and migration by glycosylphosphatidyl–inositol–anchored proteins", *Journal of Leukocyte Biology,* vol. 66, pp. 369–374, Sep. 1999.

Servant et al., "Polarization of Chemoattract Receptor Signaling During Neutrophil Chemotaxis", *Science,* vol. 287: 1037–1040, Feb. 11, 2000.

Strieter et al., "The Immunopathology of Chemotactic Cytokines: The Role of Interleukin–8 and Monocyte Chemoattractant Protein–1", *J Lab Clin Med,* 123:183–197 (1994).

Sugiyama et al., "Chemokines in Brochoalveolar Lavage Fluid in Summer–type Hypersensitivity Pneumonitis", *Eur Respir J,* 8:1084–1090 (1995).

Szekanecz et al., "Cytokines in Rheumatoid Arthritis", *Drugs and Aging,* 12:377–390, May 12, 1998.

Taub, D.D. "Chemokine–Leukocyte Interactions", *Cytokine Growth Factor Rev,* 7:355–376, (1996).

Takeya et al., "Detection of Monocyte Chemoattractant Protein–1 in Human Atherosclerotic Lesions by an Anti–monocyte Chemoattractant Protein–1 Monoclonal Antibody", *Human Pathol,* 24:534–539 (1993).

Tanaka et al., "T–cell adhesion induced by proteoglycan–immobilized cytokine MIP–1β", *Nature,* 361:79–82 (1993).

Trivedi et al., "Chemokines: Targets for novel therapeutics", *Annual Reports in Medicinal Chemistry,* 35 191–200, (2000).

Vaddi and Newton, "Comparison of biological responses of human monocytes and THP–1 cells to chemokines fo the intercrine–β family", *Journal of Leukocyte Biology,* vol. 55: 756–761, Jun. 1994.

Villiger et al., "Production of Monocyte Chemoattractant Protein–1 By Inflammed Synovial Tissue and Cultered Synoviocytes", *J Immunol,* vol. 149, pp. 722–727, (1992).

Vlodavsky et al., "Involvement of heparan sulfate and related molecules in sequestration and growth promoting activity of fibroblast growth factor", *Cancer and Mtastasis–Reviews* 15: 177–186, (1996).

Waltenberger et al., "Suramin is a Potent Inhibitor of Vascular Endothelial Growth Factor. A Contribution to the Molecular Basis of its Antianglogenic Action", *J Mol Cell Cardiol,* 28:1523–1529, (1996).

Wang et al, "Chemokines and their role in tumor growth and metastasis", *Journal of Immunological Methods,* 220:1–17, (1998).

ANTAGONISTS OF MCP-1 FUNCTION AND METHODS OF USE THEREOF

CROSS-REFERENCE TO RELATED APPLICATION

This application claims the priority under 35 USC 119(e) of U.S. Provisional Application No. 60/272,792, filed Mar. 1, 2001, which is incorporated herein by reference.

FIELD OF THE INVENTION

The present invention relates to compounds which are antagonists of MCP-1 function and are useful in the prevention or treatment of chronic or acute inflammatory or autoimmune diseases, especially those associated with aberrant lymphocyte or monocyte accumulation such as arthritis, asthma, atherosclerosis, diabetic nephropathy, inflammatory bowel disease, Crohn's disease, multiple sclerosis, nephritis, pancreatitis, pulmonary fibrosis, psoriasis, restenosis, and transplant rejection; and to pharmaceutical compositions comprising these compounds and the use of these compounds and compositions in the prevention or treatment of such diseases.

BACKGROUND OF THE INVENTION

Chemokines: Structure and Function

The migration of leukocytes from blood vessels into diseased tissues is an important process in the initiation of normal inflammatory responses to certain stimuli or insults to the immune system. However, this process is also involved in the onset and progression of life-threatening inflammatory and autoimmune diseases; blocking leukocyte recruitment in these disease states, therefore, can be an effective therapeutic strategy.

The mechanism by which leukocytes leave the bloodstream and accumulate at inflammatory sites involves three distinct steps: (1) rolling, (2) arrest and firm adhesion, and (3) transendothelial migration [Springer, Nature 346:425–433 (1990); Lawrence and Springer, Cell 65:859–873 (1991); Butcher, Cell 67:1033–1036 (1991)]. The second step is mediated at the molecular level by chemoattractant receptors on the surface of leukocytes which bind chemoattractant cytokines secreted by proinflammatory cells at the site of damage or infection. Receptor binding activates leukocytes, increases their adhesiveness to the endothelium, and promotes their transmigration into the affected tissue, where they can secrete inflammatory and chemoattractant cytokines and degradative proteases that act on the subendothelial matrix, facilitating the migration of additional leukocytes to the site of injury.

The chemoattractant cytokines, collectively known as "chemokines," are a large family of low molecular weight (8 to 10 kD) proteins that share the ability to stimulate directed cell migration ("chemotaxis") [Schall, Cytokine 3:165–183 (1991); Murphy, Rev Immun 12:593–633 (1994)].

Chemokines are characterized by the presence of four conserved cysteine residues and are grouped into two main subfamilies based on whether the two amino-terminal cysteines are separated by one amino acid (CXC subfamily, also known as α-chemokines) or immediately adjacent to each other (CC subfamily, also referred to as β-chemokines) [Baggiolini et al., Adv Immunol 55:97–179 (1994); Baggiolini et al., Annu Rev Immunol 15:675–705 (1997); Deng et al., Nature 381:661–666 (1996); Luster, New Engl J Med 338:436445 (1998); Saunders and Tarby, Drug Discovery Today 4:80–92 (1999)].

The chemokines of the CXC subfamily, represented by IL-8, are produced by a wide range of cells and act predominantly on neutrophils as mediators of acute inflammation. The CC chemokines, which include MCP-1, RANTES, MIP-1α, and MIP-1β, are also produced by a variety of cells, but these molecules act mainly on monocytes and lymphocytes in chronic inflammation.

Like many cytokines and growth factors, chemokines utilize both high and low affinity interactions to elicit full biological activity. Studies performed with labeled ligands have identified chemokine binding sites ("receptors") on the surface of neutrophils, monocytes, T cells, and eosinophils with affinities in the 500 pM to 10 nM range [Kelvin et al., J Leukoc Biol 54:604–612 (1993); Murphy, Annu Rev Immunol 12:593–633 (1994); Raport et al., J Leukoc Biol 59:18–23 (1996); Premack and Schall, Nature Med 2:1174–1178 (1996)]. The cloning of these receptors has revealed that cell surface high-affinity chemokine receptors belong to the seven transmembrane ("serpentine") G-protein-coupled receptor (GPCR) superfamily.

Chemokine receptors are expressed on different cell types, including non-leukocyte cells. Some receptors are restricted to certain cells (e.g., the CXCR1 receptor is predominantly restricted to neutrophils), whereas others are more widely expressed (e.g., the CCR2 receptor is expressed on monocytes, T cells, natural killer cells, dendritic cells, and basophils).

Given that at least twice as many chemokines have been reported to date as there are receptors, there is a high degree of redundancy in the ligands and, not surprisingly, most chemokine receptors are rather promiscuous with regard to their binding partners. For example, both MIP-1α and RANTES bind to the CCR1 and CCR5 receptors, while IL-8 binds to the CXCR1 and CXCR2 receptors. Although most chemokines receptors bind more than one chemokine, CC receptors bind only CC chemokines, and CXC receptors bind only CXC chemokines. This ligand-receptor restriction may be related to the structural differences between CC and CXC chemokines, which have similar primary, secondary, and tertiary structures, but different quaternary structures [Lodi et al., Science 263:1762–1767 (1994)].

The binding of chemokines to their serpentine receptors is transduced into a variety of biochemical and physiological changes, including inhibition of cAMP synthesis, stimulation of cytosolic calcium influx, upregulation or activation of adhesion proteins, receptor desensitization and internalization, and cytoskeletal rearrangements leading to chemotaxis [Vaddi et al., J Immunol 153:4721–4732 (1994); Szabo et al., Eur J Immunol 27:1061–1068 (1997); Campbell et al., Science 279:381–384 (1998); Aragay et al., Proc Natl Acad Sci USA 95:2985–2990 (1998); Franci et al., J Immunol 157:5606–5612 (1996); Aramori et al., EMBO J 16:4606–4616 (1997);

Haribabu et al., J Biol Chem 272:28726–28731 (1997); Newton et al., Methods Enzymol 287:174–186 (1997)]. In the case of macrophages and neutrophils, chemokine binding also triggers cellular activation, resulting in lysozomal enzyme release and generation of toxic products from the respiratory burst [Newton et al., Methods Enzymol 287:174–186 (1997); Zachariae et al., J Exp Med 171:2177–2182 (1990); Vaddi et al., J Leukocyte Biol 55:756–762 (1994)]. The molecular details of the chemokine-receptor interactions responsible for inducing signal transduction, as well as the specific pathways that link binding to the above-mentioned physiological changes, are still being elucidated. Notwithstanding the complexity of these events, it has been shown that in the case of the MCP-1/CCR2 interaction, specific molecular features of MCP-1 can induce different conformations in CCR2 that are coupled to separate post-receptor pathways [Jarnagin et al., *Biochemistry* 38:16167–16177 (1999)]. Thus, it should be possible to identify ligands that inhibit chemotaxis without affecting other signaling events.

In addition to their high-affinity seven transmembrane GPCRs, chemokines of both subfamilies bind to various extracellular matrix proteins such as the glycosaminoglycans (GAGs) heparin, chondroitin sulfate, heparan sulfate, and dermatan sulfate with affinities in the middle nanomolar to millimolar range. These low-affinity chemokine-GAG interactions are believed to be critical not only for conformational activation of the ligands and presentation to their high-affinity serpentine receptors, but also for the induction of stable chemokine gradients that may function to stimulate haptotaxis (i.e., the migration of specific cell subtypes in response to a ligand gradient that is affixed upon the surface of endothelial cells or embedded within the extracellular matrix) [Witt and Lander, *Curr Biol* 4:394–400 (1994); Rot, *Eur J Immunol* 23:303–306 (1993); Webb et al., *Proc Natl Acad Sci USA* 90:7158–7162 (1993); Tanaka et al, *Nature* 361:79–82 (1993); Gilat et al., *J Immunol* 153:4899–4906 (1994)]. Similar ligand-GAG interactions have been described for a variety of cytokines and growth factors, including the various members of the FGF family, hepatocyte growth factor, IL-3 and IL-7, GM-CSF, and VEGF [Roberts et al., *Nature* 332:376–378 (1988); Gilat et al., *Immunol Today* 17:16–20 (1996); Clarke et al., *Cytokine* 7:325–330 (1995); Miao et al., *J Biol Chem* 271:4879–4886 (1996); Vlodavsky et al., *Cancer Metastasis Rev* 15:177–186 (1996)].

MCP-1 and Diseases

Chemokines have been implicated as important mediators of allergic, inflammatory and autoimmune disorders and diseases, such as asthma, atherosclerosis, glomerulonephritis, pancreatitis, restenosis, rheumatoid arthritis, diabetic nephropathy, pulmonary fibrosis, and transplant rejection. Accordingly, it has been postulated that the use of antagonists of chemokine function may help reverse or halt the progression of these disorders and diseases.

In particular, elevated expression of MCP-1 has been observed in a number of chronic inflammatory diseases [Proost et al., *Int J Clin Lab Res* 26:211–223 (1996); Taub, D. D. *Cytokine Growth Factor Rev* 7:355–376 (1996)] including rheumatoid arthritis [Robinson et al., *Clin Exp Immunol* 101:398–407 (1995); Hosaka et al., ibid. 97:451–457 (1994); Koch et al., *J Clin Invest* 90:772–779 (1992); Villiger et al., *J Immunol* 149:722–727 (1992)], asthma [Hsieh et al., *J Allergy Clin Immunol* 98:580–587 (1996); Alam et al., *Am J Respir Crit Care Med* 153:1398-1404 (1996); Kurashima et al., *J Leukocyte Biol* 59:313–316 (1996); Sugiyarna et al., *Eur Respir J* 8:1084–1090 (1995)], and atherosclerosis [Yla-Herttuala et al., *Proc Natl Acad Sci USA* 88:5252–5256 (1991); Nelken et al., *J Clin Invest* 88:1121–1127 (1991)].

MCP-1 appears to play a significant role during the early stages of allergic responses because of its ability to induce mast cell activation and LTC4 release into the airway, which directly induces AHR (airways hyper-responsiveness) [Campbell et al., *J Immunol* 163:2160–2167 (1999)].

MCP-1 has been found in the lungs of patients with idiopathic pulmonary fibrosis and is thought to be responsible for the influx of mononuclear phagocytes and the production of growth factors that stimulate mesenchymal cells and subsequent fibrosis [Antoniades et al., *Proc Natl Acad Sci USA* 89:5371–5375 (1992)]. In addition, MCP-1 is also involved in the accumulation of monocytes in pleural effusions, which is associated with both *Mycobacterium tuberculosis* infection and malignancy [Strieter et al., *J Lab Clin Med* 123:183–197 (1994)].

MCP-1 has also been shown to be constitutively expressed by synovial fibroblasts from rheumatoid arthritis patients, and its levels are higher in rheumatoid arthritis joints compared to normal joints or those from other arthritic diseases [Koch et al., *J Clin Invest* 90:772–779 (1992)]. These elevated levels of MCP-1 are probably responsible for the monocyte infiltration into the synovial tissue. Increased levels of synovial MIP-1α and RANTES have also been detected in patients with rheumatoid arthritis [Kundel et al., *J Leukocyte Biol* 59:6–12 (1996)].

MCP-1 also plays a critical role in the initiation and development of atherosclerotic lesions. MCP-1 is responsible for the recruitment of monocytes into atherosclerotic areas, as shown by immunohistochemistry of macrophage-rich arterial wall [Yla-Herttuala et al., *Proc Natl Acad Sci USA* 88:5252–5256 (1991); Nelken et al., *J Clin Invest* 88:1121–1127 (1991)] and anti-MCP-1 antibody detection [Takeya et al., *Human Pathol* 24:534–539 (1993)]. LDL-receptor/MCP-1-deficient and apoB-transgenic/MCP-1-deficient mice show significantly less lipid deposition and macrophage accumulation throughout their aortas compared with wild-type MCP-1 strains [Alcami et al., *J Immunol* 160:624–633 (1998); Gosling et al., *J Clin Invest* 103:773–778 (1999); Gu et al., *Mol. Cell.* 2:275–281 (1998); Boring et al., *Nature* 394:894–897 (1998).

Other inflammatory diseases marked by specific site elevations of MCP-1 include multiple sclerosis (MS), glomerulonephritis, and stroke.

These findings suggest that the discovery of compounds that block MCP-1 activity would be beneficial in treating inflammatory diseases.

Antagonists of Chemokine Function

Most chemokine antagonists reported to date are either neutralizing antibodies to specific chemokines or receptor-ligand antagonists, that is, agents that compete with specific chemokines for binding to their cognate serpentine receptors but, unlike the chemokines themselves, do not activate these receptors towards eliciting a functional response [Howard et al., *Trend Biotechnol* 14:46–51 (1996)].

The use of specific anti-chemokine antibodies has been shown to curtail inflammation in a number of animal models (e.g., anti-MIP-1α in bleomycin-induced pulmonary fibrosis [Smith et al., *Leukocyte Biol* 57:782–787 (1994)]; anti-IL-8 in reperfusion injury [Sekido et al., *Nature* 365:654–657 (1995)], and anti-MCP-1 in a rat model of glomerulonephritis [Wada et al., *FASEB J* 10:1418–1425 (1996)]). In the MRL-lpr mouse arthritis model, administration of an MCP-1 antagonist significantly reduced the overall histopathological score after the early onset of the disease [Gong et al., *J Exp Med* 186:131–137 (1997)].

A major problem associated with using antibodies to antagonize chemokine function is that they must be humanized before use in chronic human diseases. Furthermore, the ability of multiple chemokines to bind and activate a single receptor forces the development of a multiple antibody strategy or the use of cross-reactive antibodies in order to completely block or prevent pathological conditions.

Several small molecule antagonists of chemokine receptor function have been reported in the scientific and patent literature [White, *J Biol Chem* 273:10095–10098 (1998); Hesselgesser, *J Biol Chem* 273:15687–15692 (1998); Bright et al., *BioorgMed Chem* Lett 8:771–774 (1998); Lapierre, *26th Natl Med Chem Symposium,* June 14–18, Richmond (Va.), USA (1998); Forbes et al., *Bioorg Med Chem* Lett 10:1803–18064 (2000); Kato et al., WO 97/24325; Shiota et al., WO 97/44329; Naya et al., WO 98/04554; Takeda Industries, JP 09–55572 (1998); Schwender et al., WO 98/02151; Hagmann et al., WO 98/27815; Connor et al., WO 98/06703; Wellington et al., U.S. Pat. No. 6,288,103].

The specificity of the chemokine receptor antagonists, however, suggests that inflammatory disorders characterized by multiple or redundant chemokine expression profiles will be relatively more refractory to treatment by these agents.

A different approach to target chemokine function would involve the use of compounds that disrupt the chemokine-GAG interaction. One class of such agents with potential therapeutic application would consist of small organic molecules that bind to the chemokine low affinity GAG-binding domain.

Compounds of this class might not inhibit binding of the chemokine to its high-affinity receptor per se, but would disrupt chemokine localization within the extracellular matrix and provide an effective block for directed leukocyte-taxis within tissues. An advantage of this strategy is the fact that most CC and CXC chemokines possess similar C-terminal protein folding domains that define the GAG-binding site, and, hence, such compounds would be more useful for the treatment of inflammatory disorders induced by multiple, functionally redundant chemokines [McFadden and Kelvin, *Biochem Pharmacol* 54:1271–1280 (1997)].

The use of small molecule drugs to bind cytokine ligands and disrupt interactions with extracellular GAGs has been reported with FGF-dependent angiogenesis [Folkman and Shing, *Adv Exp Med Biol* 313:355–364 (1992)]. For example, the heparinoids suramin and pentosan polysulphate both inhibit angiogenesis under conditions where heparin is either ineffective or even stimulatory [Wellstein and Czubayko, *Breast Cancer Res Treat* 38:109–119 (1996)]. In the case of suramin, the anti-angiogenic capacity of the drug has also been shown to be targeted against VEGF [Waltenberger et al., *J Mol Cell Cardiol* 28:1523–1529 (1996)] which, like FGF, possesses heparin-binding domains similar to those of the chemokines. Heparin or heparin sulphate has also been shown to directly compete for GAG interactions critical for T-cell adhesion mediated by MIP-1β in vitro [Tanaka et al., *Nature* 361:79–82 (1993)].

The disclosures of all documents referred to throughout this application are incorporated herein by reference.

SUMMARY OF THE INVENTION

The present invention relates to compounds that inhibit MCP-1-induced chemotaxis of human monocytic cells both in vitro and in vivo. These novel MCP-1 antagonists are useful for the treatment of inflammatory diseases, especially those associated with lymphocyte and/or monocyte accumulation, such as atherosclerosis, diabetic nephropathy, inflammatory bowel disease, Crohn's disease, multiple sclerosis, nephritis, pancreatitis, pulmonary fibrosis, psoriasis, restenosis, rheumatoid arthritis, and other chronic or acute autoimmune disorders. In addition, these compounds can be used in the treatment of allergic hypersensitivity disorders, such as asthma and allergic rhinitis, characterized by basophil activation and eosinophil recruitment.

A first embodiment of the present invention provides compounds of Formula I, Formula II, and Formula III:

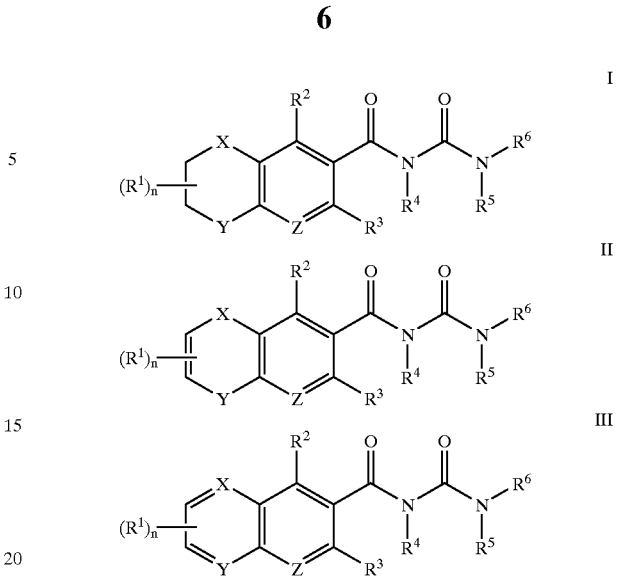

where:
n is an integer of 0 to 4 in Formula I, and is an integer of 0 to 2 in Formula, II and Formula III:
X and Y are independently O, S, CH—$R^8$, or N—$R^7$ in Formula I and Formula II, and are independently N and C—$R^8$ in Formula III;
Z is N or C—$R^8$;
provided that at least one of X, Y, and Z is a non-carbon ring atom;
each $R^1$ is independently, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —$CF_3$, halogen, nitro, —CN, —$OR^9$, —$SR^9$, —$NR^9R^{10}$, —$NR^9(CH_2)_{1-6}C(=O)OR^{10}$, —C(=O)$R^9$, —C(=O)$OR^9$, —C(=O)$NR^9R^{10}$, —OC(=O)$R^9$, —$SO_2R^9$, —$OSO_2R^9$, —$SO_2NR^9R^{10}$, —$NR^9SO_2R^{10}$ or —$NR^9C(=O)R^{10}$, wherein $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N—$(CH_2)_{1-6}C(=O)OR$ (where R is hydrogen or lower alkyl) or N-(optionally substituted $C_{1-2}$ alkyl) group, or in Formula I, n=2 and the two $R^1$'s together constitute =O,
$R^2$, $R^3$, and $R^8$ are independently, hydrogen, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —$CF_3$, halogen, nitro, —CN, —$OR^9$, —$SR^9$, —$NR^9R^{10}$, —$NR^9(CH_2)_{1-6}C(=O)OR^{10}$, —C(=O)$R^9$, —C(=O)$OR^9$, —C(=O)$NR^9R^{10}$, —OC(=O)$R^9$, —$SO_2R^9$, —$OSO_2R^9$, —$SO_2NR^9R^{10}$, —$NR^9SO_2R^{10}$ or —$NR^9C(=O)R^{10}$, wherein $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, heteroaryl, heteroaryl(lower alkyl), or $R^9$ and R[10] together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group, Each R[7] is independently, hydrogen, optionally substituted lower alkyl, alkenyl, alkynyl, cycloalkyl, cycloalkyl(lower alkyl), aryl, substituted aryl, aryl(lower alkyl), substituted aryl(lower alkyl), halo(lower alkyl), —C(=O)R[9], —C(=O)OR[9], C(=O)NR[9]R[10], —SO$_2$OR[9], —SO$_2$NR[9]R[10], wherein R[9] and R[10] are independently, hydrogen, optionally substituted lower alkyl, lower alkyl-N(C$_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, heteroaryl, heteroaryl(lower alkyl), or R[9] and R[10] together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group, R[4] and R[5] are independently, hydrogen, optionally substituted lower alkyl, optionally substituted aryl, or optionally substituted aryl(lower alkyl), or, together, are —(CH$_2$)$_{2-4}$—, R[6] is hydrogen, optionally substituted lower alkyl, alkenyl, alkynyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O)R[11], —C(=O)OR[11], —C(=O)NR[11]R[12], —SO$_2$R[11], or —SO$_2$NR[11]R[12], wherein R[11] and R[12] are independently, hydrogen, optionally substituted lower alkyl, alkenyl, alkynyl, cycloalkyl, cycloalkyl(lower alkyl), optionally substituted aryl, heteroaryl, heteroaryl(lower alkyl), or R[11] and R[12] together are —(CH$_2$)$_{4-6}$—, or a pharmaceutically acceptable salt thereof, optionally in the form of a single stereoisomer or mixture of stereoisomers thereof.

The compounds of this invention may possess one or more chiral centers, and can therefore exist as individual stereoisomers or as mixtures of stereoisomers. In addition, some of the compounds of Formula I, Formula II, and Formula III are capable of further forming pharmaceutically acceptable salts and esters. The compounds of this invention may further exist in tautomeric forms and can therefore be produced as individual tautomeric forms or as mixtures of tautomeric forms. Unless indicated otherwise, the description or naming of a compound or groups of compounds is intended to include both the individual isomers or mixtures (racemic or otherwise) of stereoisomers and their tautomeric forms. Methods for the determination of stereochemistry and the separation of stereoisomers are well known to a person of ordinary skill in the art [see the discussion in Chapter 4 of March J.: *Advanced Organic Chemistry*, 4th ed. John Wiley and Sons, New York, NY., 1992]. All of these stereoisomers and pharmaceutical forms are intended to be included within the scope of the present invention.

A second embodiment of the present invention provides compounds of Formula Ia, Formula IIa, or Formula IIIa:

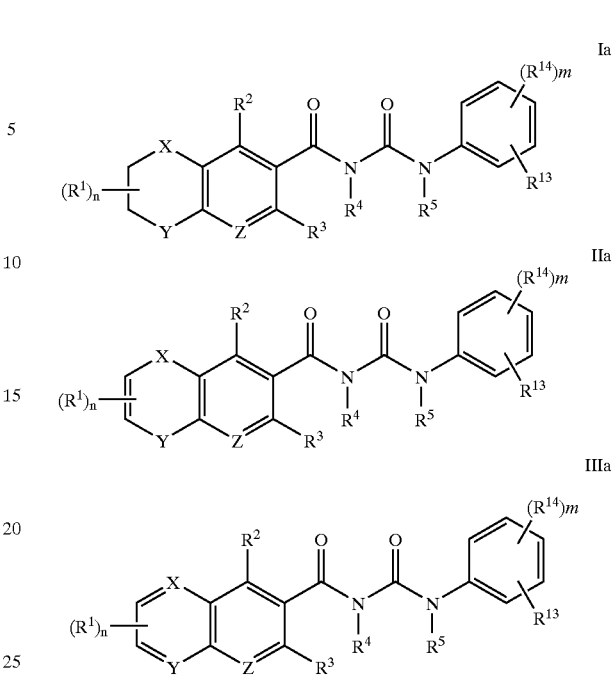

where:
m is an integer of 0 to 4;
n is an integer of 0 to 4 in Formula Ia, and is an integer of 0 to 2 in Formula IIa and Formula IIIa;
X and Y are independently O, S, CH—R[8], or N—R[7] in Formula Ia and Formula IIa, and are independently N and C—R[8] in Formula IIIa;
Z is N or C—R[8];
provided that at least one of X, Y, and Z is a non-carbon ring atom; each R[1] is independently, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —CF$_3$, halogen, nitro, —CN, —OR[9], —SR[9], —NR[9]R[10], —NR[9](CH$_2$)$_{1-6}$C(=O)OR[10], —C(=O)R[9], —C(=O)OR[9], —C(=O)NR[9]R[10], —OC(=O)R[9], —SO$_2$R[9], —OSO$_2$R[9], —SO$_2$NR[9]R[10], —NR[9]SO$_2$R[10] or —NR[9]C(=O)R[10], wherein R[9] and R[10] are independently, hydrogen, optionally substituted lower alkyl, lower alkyl-N(C$_{1-2}$ alkyl)$_2$, lower alkyl (optionally substituted heterocycloalkyl), alkenyl, alkynyl, optionally substituted cycloalkyl, cycloalkyl(lower alkyl), optionally substituted heterocycloalkyl(lower alkyl), aryl (lower alkyl), optionally substituted aryl, heteroaryl, heteroaryl(lower alkyl), or R[9] and R[10] together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group, or in Formula I, n=2 and the two R[1]'s together constitute =O, R[2], R[3] and R[8] are independently, hydrogen, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —CF$_3$, halogen, nitro, —CN, —OR[9], —SR[9], —NR[9]R[10], —NR[9]R[10], —NR[9](CH$_2$)$_{1-6}$C(=O)OR[10], —C(=O)R[9], —C(=O)OR[9], —C(=O)NR[9]R[10], —OC(=O)R[9], —SO$_2$R[9], —OSO$_2$R[9], —SO$_2$NR[9]R[10], —NR[9]SO$_2$R[10] or —NR[9]C(=O)R[10], wherein R[9] and R[10] are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N—$(CH_2)_{1-6}$C(=O)OR (where R is hydrogen or lower alkyl) or N-(optionally substituted $C_{1-2}$ alkyl) group, each $R^7$ is independently, hydrogen, optionally substituted lower alkyl, alkenyl, alkynyl, cycloalkyl, cycloalkyl (lower alkyl), aryl, substituted aryl, aryl(lower alkyl), substituted aryl(lower alkyl), halo(lower alkyl), —C(=O)$R^9$, —C(=O)O$R^9$; —C(=O)N$R^9R^{10}$, —SO$_2$O$R^9$, —SO$_2$N$R^9R^{10}$, wherein $R^9$ and $R^{10}$ are independently, hydrogen, optionally substituted lower alkyl, lower alkyl-N ($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N—$(CH_2)_{1-6}$C(=O)OR (where R is hydrogen or lower alkyl) or N-(optionally substituted $C_{1-2}$ alkyl) group, $R^4$ and $R^5$ are independently, hydrogen, lower alkyl optionally substituted lower alkyl, optionally substituted aryl, or optionally substituted aryl(lower alkyl), or, together, are —$(CH_2)_{2-4}$—, $R^{13}$ is hydrogen, optionally substituted lower alkyl, alkenyl, alkynyl, cycloalkyl, cycloalkyl(lower alkyl), heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —O$R^{15}$, —S$R^{15}$, —N$R^{15}R^{16}$, —C(=O)$R^{15}$, —C(=O)O$R^{15}$, —C(=O) N$R^{15}R^{16}$, —OC(=O)$R^{15}$, —SO$_2R^{15}$, —SO$_2$N$R^{15}R^{16}$, —N$R^{15}$SO$_2R^{16}$ or —N$R^{15}$C(=O)$R^{16}$, wherein $R^{15}$ and $R^{16}$ are independently, hydrogen, optionally substituted lower alkyl, alkenyl, alkynyl, —CF$_3$, cycloalkyl, optionally substituted heterocycloalkyl, cycloalkyl(lower alkyl), optionally substituted aryl, optionally substituted heteroaryl, optionally substituted heteroaryl(lower alkyl) or, together, are —$(CH_2)_{4-6}$— optionally interrupted by one O, S, NH or N—($C_{1-2}$ alkyl) group, and each $R^{14}$ is independently selected from optionally substituted lower alkyl, optionally substituted aryl, optionally substituted heteroaryl, hydroxy, halogen, —CF$_3$, —O$R^{17}$ —N$R^{17}R_{18}$, —C(=O)$R^{17}$, —C(=O)O$R^{17}$, —C(=O) N$R^{17}R^{18}$, wherein $R^{17}$ and $R^{18}$ are independently, hydrogen, lower alkyl, alkenyl, alkynyl, —CF$_3$, optionally substituted heterocycloalkyl, cycloalkyl, cycloalkyl(lower alkyl), optionally substituted aryl, heteroaryl, heteroaryl(lower alkyl) or, together, are —$(CH_2)_{4-6}$—, optionally interrupted by one O, S, NH or N—($C_{1-2}$ alkyl) group, or a pharmaceutically acceptable salt thereof, optionally in the form of a single stereoisomer or mixture of stereoisomers thereof.

Preferred compounds of the second embodiment are:

1. compounds of Formula Ia, where X and Y are O, Z is C—H, and n=0.
2. compounds of Formula Ia, where X and Y are O, Z is C—H, and each $R^1$ is lower alkyl.
3. compounds of Formula Ia, where X is O, Y is N—$R^7$, where $R^7$ is hydrogen or lower alkyl, Z is C—H, and each R is lower alkyl.
4. compounds of Formula Ia, where X is N—$R^7$, where $R^7$ is hydrogen or lower alkyl, Y is O, Z is C—H, and each R is lower alkyl.
5. compounds of Formula Ia, where X and Y are each N—$R^7$, where $R^7$ is hydrogen, lower alkyl, substituted lower alkyl, or optionally substituted aryl(lower alkyl), Z is C—H, and each $R^1$ is lower alkyl.
6. compounds of Formula IIIa, where X and Y are N, Z is C—H, and n=0.
7. compounds of Formula IIIa, where X and Y are N, Z is C—H, and each $R^1$ is lower alkyl.
8. compounds of the second embodiment where $R^2$ and $R^3$ are independently selected from hydrogen, lower alkyl or halogen.
9. compounds of the second embodiment where $R^4$ and $R^5$ are independently selected from hydrogen or lower alkyl.
10. compounds of the second embodiment, where $R^{13}$ is independently selected from aryl, substituted aryl, -heteroaryl or optionally substituted heteroaryl, halogen, —CF$_3$, —CN, —O$R^{15}$, or —CO$_2R^{15}$, wherein $R^{15}$ is hydrogen, lower alkyl or optionally substituted aryl.
11. compounds of the second embodiment, where each $R^{14}$ is independently selected from halogen, —CF$_3$, —OR, —CO$_2R^{17}$, or —OCH$_2$CO$_2R^{17}$, wherein $R^{17}$ is hydrogen, lower alkyl or optionally substituted aryl.

A third embodiment of the present invention provides pharmaceutical compositions comprising a pharmaceutically acceptable excipient and a therapeutically effective amount of at least one compound of this invention.

A fourth embodiment of the present invention provides methods for treating a disease treatable by the administration of an MCP-1 inhibitor, for example, chronic or acute inflammatory or autoimmune diseases such as asthma, atherosclerosis, diabetic nephropathy, glomerulonephritis, inflammatory bowel disease, Crohn's disease, multiple sclerosis, pancreatitis, pulmonary fibrosis, psoriasis, restenosis, rheumatoid arthritis, or transplant rejection, in a mammal in need thereof, comprising the administration to such mammal of a therapeutically effective amount of at least one compound of this invention or a pharmaceutically acceptable salt thereof or a pharmaceutical composition comprising the same.

A fifth embodiment of this invention provides a process for the preparation of the compounds of the invention or pharmaceutically acceptable salts thereof.

DETAILED DESCRIPTION OF THE INVENTION

Definitions

The following definitions apply to the description of compounds of the present invention:

"Alkyl" is a linear or branched saturated hydrocarbon radical having from 1 to 20 carbon atoms. Examples of alkyl radicals are: methyl, ethyl, n-propyl, isopropyl, n-butyl, isobutyl, sec-butyl, tert-butyl, n-pentyl, n-hexyl, dodecyl, etc.

"Lower alkyl", as in "lower alkyl," "lower alkoxy," "cycloalkyl(lower alkyl)," "aryl(lower alkyl)", or "heteroaryl(lower alkyl)", means a $C_{1-10}$ alkyl radical. Preferred lower alkyl radicals are those having from 1 to 6 carbon atoms.

"Alkenyl" is a linear or branched hydrocarbon radical having from 2 to 20 carbon atoms and at least one carbon-carbon double bond. Examples of alkenyl radicals are: vinyl, 1-propenyl, isobutenyl, etc.

"Alkynyl" is a linear or branched hydrocarbon radical having from 2 to 20 carbon atoms and at least one carbon-carbon triple bond. Examples of alkynyl radicals are: propargyl, 1-butynyl, etc.

"Cycloalkyl" is a monovalent cyclic hydrocarbon radical having from 3 to 12 carbon atoms. Examples of cycloalkyl radicals are: cyclopropyl, cyclobutyl, cyclopentyl, cyclohexyl, etc.

"Substituted cycloalkyl" is a monovalent cyclic hydrocarbon radical having from 3 to 12 carbon atoms, which is substituted with one, two, or three substituents each independently selected from aryl, substituted aryl, heteroaryl, halogen, —$CF_3$, nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R' or —$PO_3$HR, wherein R and R' are, independently, hydrogen, lower alkyl, cycloalkyl, aryl, substituted aryl, aryl(lower alkyl), substituted aryl(lower alkyl), heteroaryl, or heteroaryl(lower alkyl), and having 3 to 12 ring atoms, 1 to 5 of which are heteroatoms chosen, independently, from N, O, or S, and includes monocyclic, condensed heterocyclic, and condensed carbocyclic and heterocyclic rings (e.g., piperidyl, 4-morpholyl, 4-piperazinyl, pyrrolidinyl, perhydropyrrolizinyl, 1,4-diazaperhydroepinyl, etc.).

"Cycloalkyl(lower alkyl)" is a lower alkyl radical which is substituted with a cycloalkyl, as previously defined. Examples of cycloalkyl(lower alkyl) radicals are cyclopropylmethyl, cyclobutylethyl, cyclopentylmethyl, cyclohexylmethyl, etc.

"Heterocycloalkyl" is a monovalent cyclic hydrocarbon radical having 3 to 12 carbon ring atoms, 1 to 5 of which are heteroatoms chosen, independently, from N, O, or S, and includes monocyclic, condensed heterocyclic, and condensed carbocyclic and heterocyclic rings (e.g., piperidyl, 4-morpholyl, 4-piperazinyl, pyrrolidinyl, perhydropyrrolizinyl, 1,4-diazaperhydro-epinyl, etc.).

"Substituted heterocycloalkyl" is a monovalent cyclic hydrocarbon radical having from 3 to 12 carbon atoms, which is substituted with one, two, or three substituents each independently selected from aryl, substituted aryl, heteroaryl, halogen, —$CF_3$, nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R' or —$PO_3$HR, wherein R and R' are, independently, hydrogen, lower alkyl, cycloalkyl, aryl, substituted aryl, aryl(lower alkyl), substituted aryl(lower alkyl), heteroaryl, or heteroaryl(lower alkyl), and having 3 to 12 ring atoms, 1 to 5 of which are heteroatoms chosen, independently, from N, O, or S, and includes monocyclic, condensed heterocyclic, and condensed carbocyclic and heterocyclic rings (e.g., piperidyl, 4-morpholyl, 4-piperazinyl, pyrrolidinyl, perhydropyrrolizinyl, 1,4-diazaperhydroepinyl, etc.).

"Substituted heterocycloalkyl(lower alkyl)" is a lower alkyl radical which is substituted with a monovalent cyclic hydrocarbon radical having from 3 to 12 carbon atoms, which is substituted with one, two, or three substituents each independently selected from aryl, substituted aryl, heteroaryl, halogen, —$CF_3$, nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R or —$PO_3$HR, wherein R and R' are, independently, hydrogen, lower alkyl, cycloalkyl, aryl, substituted aryl, aryl(lower alkyl), substituted aryl(lower alkyl), heteroaryl, or heteroaryl(lower alkyl), and having 3 to 12 ring atoms, 1 to 5 of which are heteroatoms chosen, independently, from N, O, or S, and includes monocyclic, condensed heterocyclic, and condensed carbocyclic and heterocyclic rings (e.g., piperidyl, 4-morpholyl, 4-piperazinyl, pyrrolidinyl, perhydropyrrolizinyl, 1,4-diazaperhydro-epinyl, etc.).

"Substituted alkyl" or "substituted lower alkyl," is an alkyl or lower alkyl radical, respectively, which is substituted with one, two, or three substituents each independently selected from aryl, substituted aryl, heteroaryl, halogen, —$CF_3$, nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R' or —$PO_3$HR, wherein R and R' are, independently, hydrogen, lower alkyl, cycloalkyl, aryl, substituted aryl, aryl(lower alkyl), substituted aryl(lower alkyl), heteroaryl, or heteroaryl(lower alkyl).

"Halo(lower alkyl)" is a radical derived from lower alkyl containing at least one halogen substituent. Non-limiting examples of halo-lower alkyl radicals include: —$CF_3$, —$C_2F_5$, etc.

"Aryl", as in "aryl", "aryloxy", and "aryl(lower alkyl)", is a radical derived from an aromatic hydrocarbon containing 6 to 16 ring carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). Preferred aryl radicals are those containing from 6 to 14 carbon atoms.

"Substituted aryl" is an aryl radical which is substituted with one, two, or three substituents each independently selected from alkyl, substituted alkyl, halo(lower alkyl), halogen, nitro, —CN, —OR, —SR, —NRR', —C(=O)R, —OC(=O)R, —C(=O)OR, —$SO_2$OR, —$OSO_2$R, —$SO_2$NRR', —$PO_3H_2$, —$NRSO_2$R', —C(=O)NRR', or NRC(=O)R', wherein R and R' are, independently, hydrogen, lower alkyl, substituted lower alkyl, cycloalkyl, aryl, substituted aryl, aryl(lower alkyl), substituted aryl (lower alkyl), heteroaryl, or heteroaryl(lower alkyl). Preferred substituted aryl radicals are those substituted with one, two, or three substituents each independently selected from the group consisting of lower alkyl, halogen, —$CF_3$, nitro, —CN, —OR, —NRR', C(=O)NRR', —$SO_2$OR, —$SO_2$NRR', —$PO_3H_2$, —$NRSO_2$R', or —NRC(=O)R'.

"Heteroaryl", as in "heteroaryl" and "heteroaryl(lower alkyl)", is a radical derived from an aromatic hydrocarbon containing 5 to 14 ring atoms, 1 to 5 of which are heteroatoms chosen, independently, from N, O, or S, and includes monocyclic, condensed heterocyclic, and condensed carbocyclic and heterocyclic aromatic rings (e.g., thienyl, furyl, pyrrolyl, pyrimidinyl, isoxazolyl, oxazolyl, indolyl, isobenzofuranyl, purinyl, isoquinolyl, pteridinyl, imidazolyl, pyridyl, pyrazolyl, pyrazinyl, quinolyl, etc.).

"Substituted heteroaryl" is a heteroaryl radical which is substituted with one, two, or three substituents each independently selected from alkyl, substituted alkyl, halogen, —$CF_3$, nitro, —CN, —OR, —SR, —NRR', —C(=O)R, OC(=O)R, —C(=O)OR, —$SO_2$OR, —$OSO_2$R, —$SO_2$NRR', —$NRSO_2$R', —C(=O)NRR', or —NRC(=O) R', wherein R and R' are, independently, hydrogen, lower alkyl, substituted lower alkyl, cycloalkyl, aryl, substituted aryl, aryl(lower alkyl), substituted aryl(lower alkyl), heteroaryl, or heteroaryl(lower alkyl). Particularly preferred substituents on the substituted heteroaryl moiety include lower alkyl, substituted lower alkyl, halo-lower-alkyl, halogen, nitro, —CN, —OR, —SR, and —NRR'.

"Aryl(lower alkyl)" is a lower alkyl radical which is substituted with an aryl, as previously defined.

"Substituted aryl(lower alkyl)" is an aryl(lower alkyl) radical having one to three substituents on either or both of the aryl and the alkyl portion of the radical.

"Heteroaryl(lower alkyl)" is a lower alkyl radical which is substituted with a heteroaryl, as previously defined.

"Substituted heteroaryl(lower alkyl)" is a heteroaryl (lower alkyl) radical having one to three substituents on the heteroaryl portion or the alkyl portion of the radical, or both.

"Lower alkoxy" is an —OR radical, where R is a lower alkyl or cycloalkyl.

"Halogen" means fluoro, chloro, bromo, or iodo.

"Tautomers" are isomeric compounds that differ from one another by interchanged positions of a and n bonds. The compounds are in equilibrium with one another. They may also differ from one another in the position at which a hydrogen atom is attached.

"Inner salts" or "Zwitterions" are compounds wherein the positive and negative groups, such as amine and acid groups within the compound, are equally ionized. The compounds are charge separated species that result from the transfer of a proton from the acidic site to a basic site, typically in a compound containing an amine and an acid group.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts and esters" means any salt and ester=that is pharmaceutically acceptable and has the desired pharmacological properties. Such salts include salts that may be derived from an inorganic or organic acid, or an inorganic or organic base, including amino acids, which is not toxic or undesirable in any way. Suitable inorganic salts include those formed with the alkali metals, e.g., sodium and potassium, magnesium, calcium, and aluminum. Suitable organic salts include those formed with organic bases such as the amnine bases, e.g., ethanolamine, diethanolamnine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane and arene-sulfonic acids such as methanesulfonic acid and benzenesulfonic acid). Pharmaceutically acceptable esters include esters formed from carboxy, sulfonyloxy, and phosphonoxy groups present in the compounds, e.g., C1–6 alkyl esters. When there are two acidic groups present, a pharmaceutically acceptable salt or ester may be a mono-acid-mono-salt or ester or a di-salt or ester; and similarly, where there are more than two acidic groups present, some or all of such groups can be salified or esterified.

"Therapeutically effective amount" means that amount which, when administered to a mammal for treating a disease, is sufficient to effect such treatment for the disease.

"Treating" or "treatment" of a disease in a mammal includes:

(1) Preventing the disease from occurring in a mammal which may be predisposed to the disease but does not yet experience or display symptoms of the disease;
(2) Inhibiting the disease, i.e., arresting its development, or
(3) Relieving the disease, i.e., causing regression of the disease.

"Disease" includes any unhealthy condition of an animal (which includes human and non-human mammals), including particularly various forms of inflammatory illnesses or diseases, such as asthmia, atherosclerosis, diabetic nephropathy, glomerulonepliritis, inflammatory bowel disease, Crohn's disease, multiple sclerosis, pancreatitis, pulmonary fibrosis, psoriasis, restenosis, rheumatoid arthritis, immune disorders, and transplant rejection.

The compounds of this invention may possess one or more chiral centers, and can therefore be produced as individual stereoisomers or as mixtures of stereoisomers, depending on whether individual stereo isomers or mixtures of stereoisomers of the starting materials are used. Unless indicated otherwise, the description or naming of a compound or groups of compounds is intended to include both the individual isomers or mixtures (racemic or otherwise) of stereoisomers. Methods for the determination of stereochemistry and the separation of stereoisomers are well known to a person of ordinary skill in the art [see the discussion in Chapter 4 of March J.: *Advanced Organic Chemistry*, 4th ed. John Wiley and Sons, New York, N.Y., 1992].

Compounds and Pharmaceutically Acceptable Salts

A first embodiment of the present invention provides compounds of Formula I, Formula II, and Formula III:

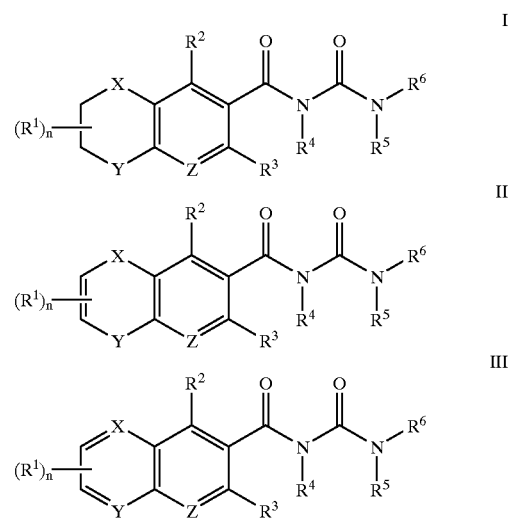

where n, X, Y, Z and $R^1$ to $R^8$ are as defined in the Summary of the Invention.

Where $R^9$ and $R^{10}$ together are —$(CH_2)_{4-6}$— optionally interrupted by one O, S, NH, N-(aryl), N-(aryl(lower alkyl)), N—$(CH_2)_{1-6}C(=O)OR$ (where R is hydrogen or lower alkyl) or N-(optionally substituted $C_{1-2}$ alkyl) group, examples include piperazinyl, 4-methylpiperazinyl, 4-morpholyl, and hexahydropyrimidyl.

Preferably, X and Y are independently O or N—$R^7$ in Formula I and Formula II.

Preferably, $R^1$ is optionally substituted lower alkyl, optionally substituted heterocycloalkyl, optionally substituted aryl, optionally substituted heteroaryl, optionally substituted aryl(lower alkyl), halogen, —$OR^9$, —$NR^9R^{10}$, —$C(=O)OR^9$, —$C(=O)NR^9R^{10}$, —$SO_2NR^9R^{10}$, or —$NR^9C(=O)R^{10}$, wherein $R^9$ and $R^{10}$ are independently, hydrogen, optionally substituted lower alkyl, lower alkyl-N ($C_{1-2}$ alkyl)$_2$, lower alkyl(optionally substituted heterocycloalkyl), aryl(lower alkyl), optionally substituted aryl, heteroaryl, or heteroaryl(lower alkyl).

More preferably, n is 0.

Preferably, $R^2$ is hydrogen, optionally substituted lower alkyl, cycloalkyl, optionally substituted heterocycloalkyl, optionally substituted aryl, optionally substituted heteroaryl, optionally substituted aryl(lower alkyl), halogen, —$OR^9$, —NR$^9$(CH$_2$)$_{1-6}$C(=O)OR$^{10}$, —C(=O)OR$^9$, —C(=O)NR$^9$R$^{10}$, —SO$_2$NR$^9$R$^{10}$, or —NR$^9$C(=O)R$^{10}$, wherein R$^9$ and R$^{10}$ are independently, hydrogen, optionally substituted lower alkyl, lower alkyl-N(C$_{1-2}$ alkyl)$_2$, lower alkyl (optionally substituted heterocycloalkyl), optionally substituted cycloalkyl, cycloalkyl(lower alkyl), optionally substituted aryl, heteroaryl, heteroaryl(lower alkyl), or R$^9$ and R$^{10}$ together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group.

More preferably, R$^2$ is optionally substituted lower alkyl, cycloalkyl, optionally substituted heterocycloalkyl, optionally substituted aryl, optionally substituted heteroaryl, optionally substituted aryl(lower alkyl), halogen, —OR$^9$, —NR$^9$(CH$_2$)$_{1-6}$C(=O)OR$^{10}$, —C(=O)OR$^9$, —C(=O)NR$^9$R$^{10}$, —SO$_2$NR$^9$R$^{10}$, or —NR$^9$C(=O)R$^{10}$, wherein R$^9$ and R$^{10}$ are independently, hydrogen, optionally substituted lower alkyl, lower alkyl-N(C$_{1-2}$ alkyl)$_2$, lower alkyl (optionally substituted heterocycloalkyl), optionally substituted cycloalkyl, cycloalkyl(lower alkyl), optionally substituted aryl, heteroaryl, heteroaryl(lower alkyl), or R$^9$ and R$^{10}$ together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group.

Preferably, R$^3$ is hydrogen, optionally substituted lower alkyl, optionally substituted heterocycloalkyl, optionally substituted aryl, optionally substituted heteroaryl, optionally substituted aryl(lower alkyl), halo(lower alkyl), halogen, —OR$^9$, —NR$^9$R$^{10}$, —C(=O)OR$^9$, or —C(=O)NR$^9$R$^{10}$, wherein R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, heteroaryl, heteroaryl(lower alkyl), or R$^9$ and R$^{10}$ together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group.

More preferably, R$^3$ is optionally substituted lower alkyl, optionally substituted heterocycloalkyl, optionally substituted aryl, optionally substituted heteroaryl, optionally substituted aryl(lower alkyl), halo(lower alkyl), halogen, —OR$^9$, —NR$^9$R$^{10}$, —C(=O)OR$^9$, or —C(=O)NR$^9$R$^{10}$, wherein R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, heteroaryl, heteroaryl(lower alkyl), or R$^9$ and R$^{10}$ together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group.

Preferably, each R$^7$ is independently, hydrogen, optionally substituted lower alkyl, optionally substituted heterocycloalkyl, optionally substituted aryl, optionally substituted heteroaryl, optionally substituted aryl(lower alkyl), —C(=O)R$^9$, —C(=O)OR$^9$, —C(=O)NR$^9$R$^{10}$, —SO$_2$R$^9$, or —SO$_2$NR$^9$R$^{10}$, wherein R$^9$ and R$^{10}$ are independently, hydrogen, optionally substituted lower alkyl, lower alkyl-N(C$_{1-2}$ alkyl)$_2$, alkenyl, alkynyl, optionally substituted cycloalkyl, cycloalkyl(lower alkyl), optionally substituted aryl, heteroaryl, or heteroaryl(lower alkyl).

Preferably, R$^8$ is hydrogen, optionally substituted lower alkyl, optionally substituted heterocycloalkyl, optionally substituted aryl, optionally substituted heteroaryl, optionally substituted aryl(lower alkyl), halo(lower alkyl), —CF$_3$, halogen, —OR$^9$, —NR$^9$R$^{10}$, —C(=O)R$^9$, —C(=O)OR$^9$, —C(=O)NR$^9$R$^{10}$, —OC(=O)R$^9$, —SO$_2$R$^9$, —SO$_2$NR$^9$R$^{10}$, —NR$^9$SO$_2$R$^{10}$ or —NR$^9$C(=O)R$^{10}$, wherein R$^9$ and R$^{10}$ are independently, hydrogen, optionally substituted lower alkyl, lower alkyl-N(C$_{1-2}$ alkyl)$_2$, optionally substituted cycloalkyl, cycloalkyl(lower alkyl), optionally substituted aryl, heteroaryl, heteroaryl(lower alkyl), or R$^9$ and R$^{10}$ together are —(CH$_2$)$_{4-6}$— optionally interrupted by one O, S, NH, N-(aryl), N-(aryl(lower alkyl)), N—(CH$_2$)$_{1-6}$C(=O)OR (where R is hydrogen or lower alkyl) or N-(optionally substituted C$_{1-2}$ alkyl) group.

Preferably, R$^4$ and R$^5$ are independently, hydrogen or lower alkyl, or together are —(CH$_2$)$_{2-4}$—. More preferably, R$^4$ and R$^5$ are independently, hydrogen or lower alkyl.

Preferably, R$^6$ is hydrogen, optionally substituted lower alkyl, alkenyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O)R$^{11}$, —C(=O)OR$^{11}$, —C(=O)NR$^{11}$R$^{12}$, —SO$_2$R$^{11}$, or —SO$_2$NR$^{11}$R$^{12}$, wherein R$^{11}$ and R$^{12}$ are independently, hydrogen, optionally substituted lower alkyl, cycloalkyl, cycloalkyl(lower alkyl), aryl, heteroaryl, heteroaryl(lower alkyl), or R$^{11}$ and R$^{12}$ together are —(CH$_2$)$_{4-6}$—.

A particular preferred "substituted aryl" is a phenyl group substituted with a R$^{13}$ and optionally substituted with up to four R$^{14}$s, where R$^{13}$ and R$^{14}$ are defined with respect to Formulae Ia, Ia, and IIIa.

The above-listed preferences equally apply for the compounds of Formulae Ia, IIa and IIIa, below.

In a more preferred version of the first embodiment of the invention,

Y is N—R$^7$ and Z is C—R$^8$ for Formulae I and II,

R$^1$ is lower alkyl,

R$^4$ and R$^5$ are hydrogen, and

R$^6$ is hydrogen, optionally substituted lower alkyl, alkenyl, alkynyl, cycloalkyl, cycloalkyl(lower alkyl), optionally substituted heterocycloalkyl, optionally substituted aryl, aryl(lower alkyl), optionally substituted heteroaryl, optionally substituted heteroaryl(lower alkyl), halo(lower alkyl), —C(=O)R$^{11}$, —C(=O)OR$^{11}$, —C(=O)NR$^{11}$R$^{12}$, —SO$_2$R$^{11}$, or —SO$_2$NR$^{11}$R$^{12}$, wherein R$^{11}$ and R$^{12}$ are independently, hydrogen, optionally substituted lower alkyl, alkenyl, alkynyl, cycloalkyl, cycloalkyl(lower alkyl), optionally substituted aryl, heteroaryl, heteroaryl (lower alkyl), or R$^{11}$ and R$^{12}$ together are —(CH$_2$)$_{4-6}$—, or a pharmaceutically acceptable salt thereof, optionally in the form of a single stereoisomer or mixture of stereoisomers thereof.

More preferably still, R$^2$ is —NR$^9$R$^{10}$, wherein R$^9$ and R$^{10}$ are independently, hydrogen, optionally substituted lower alkyl, lower alkyl-N(C$_{1-2}$ alkyl)$_2$, lower alkyl (optionally substituted heterocycloalkyl), alkenyl, alkynyl, optionally substituted cycloalkyl, cycloalkyl(lower alkyl), benzyl, optionally substituted aryl, heteroaryl, heteroaryl (lower alkyl), or R$^9$ and R$^{10}$ together are —(CH$_2$)$_{4-6}$— optionally interrupted by one O, S, NH, N-(aryl), N-(aryl (lower alkyl)), N—(CH$_2$)$_{1-6}$C(=O)OR (where R is hydrogen or lower alkyl) or N-(optionally substituted C$_{1-2}$ alkyl) group.

In another more preferred version of the first embodiment of the invention,

Y is N—R$^7$ and Z is C—R$^8$ in Formuale I and II,

R$^1$ and R$^8$ are lower alkyl,

R$^2$ is —NR$^9$R$^{10}$, $R^4$ and $R^5$ are hydrogen, and $R^6$ is hydrogen, optionally substituted lower alkyl, alkenyl, alkynyl, cycloalkyl, cycloalkyl(lower alkyl), optionally substituted heterocycloalkyl, optionally substituted aryl, aryl(lower alkyl), optionally substituted heteroaryl, optionally substituted heteroaryl(lower alkyl), halo(lower alkyl), —C(=O)$R^{11}$, —C(=O)O$R^{11}$, —C(=O)N$R^{11}R^{12}$, —SO$_2R^{11}$, or —SO$_2$N$R^{11}R^{12}$, wherein $R^{11}$ and $R^{12}$ are independently, hydrogen, optionally substituted lower alkyl, alkenyl, alkynyl, cycloalkyl, cycloalkyl(lower alkyl), optionally substituted aryl, heteroaryl, heteroaryl (lower alkyl), or $R^{11}$ and $R^{12}$ together are —(CH$_2$)$_{4-6}$—, or a pharmaceutically or a pharmaceutically acceptable salt thereof, optionally in the form of a single stereoisomer or mixture of stereoisomers thereof.

The second embodiment of the present invention provides compounds of Formulae Ia, IIa or IIIa:

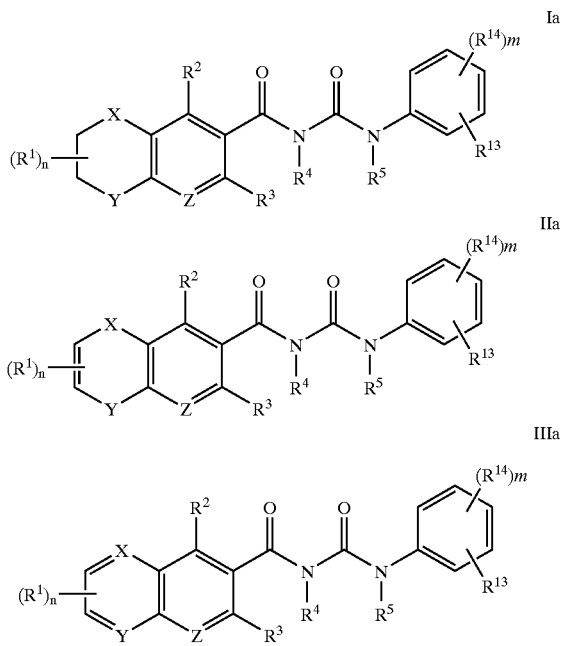

wherein:

Y is O, S or N—$R^7$ in Formulae Ia and IIa,

X and Y are independently N and C—$R^7$ in Formula IIIa,

Z is N or C—$R^8$, $R^1$, $R^2$, $R^3$, $R^4$, $R^5$, $R^7$ and $R^8$ are as defined in the first embodiment, $R^{13}$ is hydrogen, optionally substituted lower alkyl, alkenyl, alkynyl, cycloalkyl, cycloalkyl(lower alkyl), heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —O$R^{15}$,—S$R^{15}$, —N$R^{15}R^{16}$, —C(=O)$R^{15}$, —C(=O)O$R^{15}$, —C(=O)N$R^{15}R^{16}$, —OC(=O)$R^{15}$, —SO$_2R^{15}$, —SO$_2$N$R^{15}R^{16}$, —N$R^{15}$SO$_2R^{16}$ or —N$R^{15}$C(=O)$R^{16}$, wherein $R^{15}$ and $R^{16}$ are independently, hydrogen, optionally substituted lower alkyl, alkenyl, alkynyl, —CF$_3$, cycloalkyl, optionally substituted heterocycloalkyl, cycloalkyl(lower alkyl), optionally substituted aryl, optionally substituted heteroaryl, optionally substituted heteroaryl(lower alkyl), or, together, are —(CH$_2$)$_{4-6}$— optionally interrupted by one O, S, NH or N—(C$_{1-2}$ alkyl) group, and each $R^{14}$ is independently selected from optionally substituted lower alkyl, optionally substituted aryl, optionally substituted heteroaryl, hydroxy, halogen, —CF$_3$,—O$R^{17}$ —N$R^{17}R^{18}$, —C(=O)$R^{17}$, —C(=O)O$R^{17}$, —C(=O)N$R^{17}R^{18}$, wherein $R^{17}$ and $R^{18}$ are independently, hydrogen, lower alkyl, alkenyl, alkynyl, —CF$_3$, optionally substituted heterocycloalkyl, cycloalkyl, cycloalkyl(lower alkyl), optionally substituted aryl, heteroaryl, heteroaryl(lower alkyl), or, together, are —(CH$_2$)$_{4-6}$—, optionally interrupted by one O, S, NH or N—(C$_{1-2}$ alkyl) group, or a pharmaceutically acceptable salt thereof as a single stereoisomer or mixture of stereoisomers.

Wherein $R^{13}$ is —O$R^{15}$, and $R^{15}$ is optionally substituted lower alkyl, where it may, for example, be optionally substituted with —C(=O)O$R^{19}$, wherein $R^{19}$ is hydrogen or lower alkyl.

Where $R^9$ and $R^{10}$ together are —(CH$_2$)$_{4-6}$— optionally interrupted by one O, S, NH or N—(C$_{1-2}$ alkyl) group, examples include piperazinyl, 4-methylpiperazinyl, morpholyl, and hexahydropyrimidyl.

n is a stereocompatible integer of 0 to 4. The term "stereocompatible" limits the number of substituents permissible by available valences in accordance with space requirements of substituents, among other.

Preferably, $R^{13}$ is hydrogen, optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —O$R^{15}$, —S$R^{15}$, —N$R^{15}R^{16}$, —C(=O)$R^{15}$, —C(=O)O$R^{15}$, —C(=O)N$R^{15}R^{16}$, —OC(=O)$R^{15}$, —SO$_2R^{15}$, —SO$_2$N$R^{15}R^{16}$, or —N$R^{15}$C(=O)$R^{16}$, wherein $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —(CH$_2$)$_{4-6}$— optionally interrupted by one O, S, NH or N—(C$_{1-2}$ alkyl) group.

More preferably, $R^{13}$ is optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —O$R^{15}$, —S$R^{15}$, —N$R^{15}R^{16}$, —C(=O)$R^{15}$, —C(=O)O$R^{15}$, —C(=O)N$R^{15}R^{16}$, —OC(=O)$R^{15}$, —SO$_2R^{15}$, —SO$_2$N$R^{15}R^{16}$, or —N$R^{15}$C(=O)$R^{16}$, wherein $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —(CH$_2$)$_{4-6}$— optionally interrupted by one O, S, NH or N—(C$_{1-2}$ alkyl) group.

Preferably, $R^{14}$ is independently selected from optionally substituted lower alkyl, optionally substituted aryl, optionally substituted heteroaryl, hydroxy, halogen, —CF$_3$, —O$R^{17}$, —N$R^{17}R^{18}$, —C(=O)$R^{17}$, —C(=O)O$R^{17}$, —C(=O)N$R^{17}R^{18}$, wherein $R^{17}$ and $R^{18}$ are, independently, hydrogen, lower alkyl, alkenyl, or optionally substituted aryl.

Preferably, where $R^{13}$ is not hydrogen, n is an integer of 1 to 2. More preferably, where $R^{13}$ is not hydrogen, n is 1.

In another more preferred version of the second embodiment of the invention,

Y is N—$R^7$ and Z is C—$R^8$ for Formulae Ia and IIa, $R^1$ is lower alkyl, $R^2$ is —N$R^9R^{10}$, wherein $R^9$ and $R^{10}$ are independently, hydrogen, optionally substituted lower alkyl, lower alkyl-N $(C_{1-2}$ alkyl$)_2$, lower alkyl(optionally substituted heterocycloalkyl), alkenyl, alkynyl, optionally substituted cycloalkyl, cycloalkyl(lower alkyl), benzyl, optionally substituted aryl, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N—$(CH_2)_{1-6}$C(=O)OR (where R is hydrogen or lower alkyl) or N-(optionally substituted $C_{1-2}$ alkyl) group such as piperazinyl, 4-methylpiperazinyl, 4-morpholyl, hexahydropyrimidyl, and $R^{13}$ is hydrogen, optionally substituted lower alkyl, alkenyl, alkynyl, cycloalkyl, cycloalkyl(lower alkyl), heterocycloalkyl, optionally substituted aryl, aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —OC$(=O)R^{15}$, —$SO_2R^{15}$, —$SO_2NR^{15}R^{16}$, —$NR^{15}SO_2R^{16}$ or —$NR^{15}C(=O)R^{16}$, wherein $R^{15}$ and $R^{16}$ are independently, hydrogen, lower alkyl, alkenyl, alkynyl, —$CF_3$, cycloalkyl, optionally substituted heterocycloalkyl, cycloalkyl(lower alkyl), optionally substituted aryl, optionally substituted heteroaryl, optionally substituted heteroaryl(lower alkyl) or $R^{15}$ and $R^{16}$ together are —$(CH_2)_{4-6}$— optionally interrupted by one O, S, NH or N—$(C_{1-2}$ alkyl) group.

More preferably still, $R^4$ and $R^5$ are hydrogen.

A particular preferred "substituted aryl" is a phenyl group substituted with a $R^{13}$ and optionally substituted with up to four $R^{14}$s, where $R^{13}$ and $R^{14}$ are defined with respect to Formulae Ia, IIa and IIIa.

Wherein $R^{13}$ is —$OR^{15}$, and $R^{15}$ is optionally substituted lower alkyl, it may, for example, be optionally substituted with —$C(=O)OR^{19}$, wherein $R^{19}$ is hydrogen or lower alkyl.

Where $R^9$ and $R^{10}$ together are —$(CH_2)_{4-6}$— optionally interrupted by one O, S, NH or N—$(C_{1-2}$ alkyl) group, examples include piperazinyl, 4-methylpiperazinyl, morpholyl, and hexahydropyrimidyl.

m is a stereocompatible integer of 0 to 4. The term "stereocompatible" limits the number of substituents permissible by available valences in accordance with space requirements of substituents, among other.

Preferably, $R^{13}$ is hydrogen, optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —$OC(=O)R^{15}$, —$SO_2R^{15}$, —$SO_2NR^{15}R^{16}$, or —$NR^{15}C(=O)R^{16}$, wherein $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —$(CH_2)_{4-6}$— optionally interrupted by one O, S, NH or N—$(C_{1-2}$ alkyl) group.

More preferably, $R^{13}$ is optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —$OC(=O)R^{15}$, —$SO_2R^{15}$, —$SO_2NR^{15}R^{16}$, or —$NR^{15}C(=O)R^{16}$, wherein $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —$(CH_2)_{4-6}$— optionally interrupted by one O, S, NH or N—$(C_{1-2}$ alkyl) group.

Preferably, $R^{14}$ is independently selected from optionally substituted lower alkyl, optionally substituted aryl, optionally substituted heteroaryl, hydroxy, halogen, —$CF_3$, —$OR^{17}$, —$NR^{17}R^{18}$, —$C(=O)R^{17}$, —$C(=O)OR^{17}$, —$C(=O)NR^{17}R^{18}$, wherein $R^{17}$ and $R^{18}$ are, independently, hydrogen, lower alkyl, alkenyl, or optionally substituted aryl.

Preferably, where $R^{13}$ is not hydrogen, m is an integer of 1 to 2. More preferably, where $R^{13}$ is not hydrogen, m is 1.

In another more preferred version of the second embodiment of the invention,

Z is C—$R^8$ $R^1$ is lower alkyl, $R^2$ is —$NR^9R^{10}$, wherein $R^9$ and $R^{10}$ are independently, hydrogen, optionally substituted lower alkyl, lower alkyl-N$(C_{1-2}$ alkyl$)_2$, lower alkyl(optionally substituted heterocycloalkyl), alkenyl, alkynyl, optionally substituted cycloalkyl, cycloalkyl(lower alkyl), benzyl, optionally substituted aryl, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N—$(CH_2)_{1-6}$C(=O)OR (where R is hydrogen or lower alkyl) or N-(optionally substituted $C_{1-2}$ alkyl) group such as piperazinyl, 4-methylpiperazinyl, 4-morpholyl, hexahydropyrimidyl, and $R^{13}$ is hydrogen, optionally substituted lower alkyl, alkenyl, alkynyl, cycloalkyl, cycloalkyl(lower alkyl), heterocycloalkyl, optionally substituted aryl, aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —OC$(=O)R^{15}$, —$SO_2R^{15}$, —$SO_2NR^{15}R^{16}$, —$NR^{15}SO_2R^{16}$ or —$NR^{15}C(=O)R^{16}$, wherein $R^{15}$ and $R^{16}$ are independently, hydrogen, lower alkyl, alkenyl, alkynyl, —$CF_3$, cycloalkyl, optionally substituted heterocycloalkyl, cycloalkyl(lower alkyl), optionally substituted aryl, optionally substituted heteroaryl, optionally substituted heteroaryl(lower alkyl) or $R^{15}$ and $R^{16}$ together are —$(CH_2)_{4-6}$— optionally interrupted by one O, S, NH or N—$(C_{1-2}$ alkyl) group.

The above-listed preferences for the compounds of Formulae I, II, and III equally apply for the compounds of Formulae Ia, IIa and IIIa.

In addition, certain compounds of the invention may contain one or more chiral centers. In such cases, all stereoisomers also fall within the scope of this invention. The invention compounds include the individually isolated stereoisomers as well as mixtures of such stereoisomers.

Some of the compounds of Formula I, Formula II, and Formula III are capable of further forming pharmaceutically acceptable salts and esters. All of these forms are included within the scope of the present invention.

Pharmaceutically acceptable base addition salts of the compounds of Formula I, Formula II, and Formula III include salts which may be formed when acidic protons present in the parent compound are capable of reacting with inorganic or organic bases. Typically, the parent compound is treated with an excess of an alkaline reagent, such as hydroxide, carbonate or alkoxide, containing an appropriate cation. Cations such as $Na^+$, $K^+$, $Ca^{2+}$ and $NH_4^+$ are examples of cations present in pharmaceutically acceptable salts. The $Na^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as choline, dicyclohexylamine, ethylenediamine, ethanolamine, diethanolamine, triethanolamine, procaine, N-methylglucamine and the like [for a nonexclusive list see, for example, Berge et al., "Pharmaceutical Salts," *J. Pharma. Sci.* 66:1 (1977)]. The free acid form may be regenerated by contacting the base addition salt with an acid and isolating the free acid in the conventional manner. The free acid forms can differ from their respective salt forms somewhat in certain physical properties such as solubility in polar solvents.

Pharmaceutically acceptable acid addition salts of the compounds of Formula I, Formula II, and Formula III include salts which may be formed when the parent compound contains a basic group. Acid addition salts of the compounds are prepared in a suitable solvent from the parent compound and an excess of a non-toxic inorganic acid, such as hydrochloric acid, hydrobromic acid, sulfuric acid (giving the sulfate and bisulfate salts), nitric acid, phosphoric acid and the like, or a non-toxic organic acid such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methylbicyclo[2.2.2.]oct-2-ene-1-carboxylic acid, glucoheptonic acid, gluconic acid, 4,4-methylenebis(3-hydroxy-2-naphthoic) acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid and the like. The free base form may be regenerated by contacting the acid addition salt with a base and isolating the free base in the conventional manner. The free base forms can differ from their respective salt forms somewhat in certain physical properties such as solubility in polar solvents.

Also included in the embodiment of the present invention are salts of amino acids such as arginate and the like, gluconate, and galacturonate [see Berge, supra (1977)].

Some of the compounds of the invention may form inner salts or Zwitterions.

Certain of the compounds of the present invention can exist in unsolvated forms as well as solvated forms, including hydrated forms, and are intended to be encompassed within the scope of the present invention.

Certain of the compounds of the present invention may also exist in one or more solid or crystalline phases or polymorphs; the variable biological activities of such polymorphs or mixtures of such polymorphs are also included in the scope of this invention.

Some preferred compounds of the present invention are those listed in Table 11.

Pharmaceutical Compositions

A third embodiment of the present invention provides pharmaceutical compositions comprising a pharmaceutically acceptable excipient and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate.

Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Some specific examples of suitable pharmaceutical compositions are described in the examples.

Typically, a pharmaceutical composition of the present invention is packaged in a container with a label indicating the use of the pharmaceutical composition in the treatment of a disease such as asthma, atherosclerosis, glomerulonephritis, pancreatitis, restenosis, rheumatoid arthritis, multiple sclerosis, diabetic nephropathy, pulmonary fibrosis, and transplant rejection, or a chronic or acute immune disorder, or a combination of any of these disease conditions.

Methods of Use

A fourth embodiment of the present invention provides a method for treating a disease treatable by administration of an MCP-1 inhibitor, for example, a chronic or acute inflammatory disease such as asthma, atherosclerosis, diabetic nephropathy, glomerulonephritis, inflammatory bowel disease, Crohn's disease, multiple sclerosis, pancreatitis, pulmonary fibrosis, psoriasis, restenosis, rheumatoid arthritis, or a chronic or acute immune disorder, or transplant rejection in a mammal in need thereof, comprising the administration to such mammal of a therapeutically effective amount of at least one compound of general Formula I, Formula II and Formula III or pharmaceutically acceptable salts and esters thereof.

The compounds of the present invention inhibit chemotaxis of a human monocytic cell line (THP-1 cells) induced by human MCP-1 in vitro. This inhibitory effect has also been observed in vivo. Indeed, the compounds have been shown to reduce monocyte infiltration in a thioglycollate-induced inflammation model in mice.

The compounds of the present invention have been found to prevent the onset or ameliorate symptoms in several animal models of inflammation. For example, the compounds inhibited recruitment of monocytes into the glomeruli in an anti-Thy-1 antibody-induced model of nephritis; reduced paw swelling in a rat model of adjuvant arthritis; inhibited neointimal hyperplasia after balloon injury in a rat model of restenosis, and reduced the amount of lesion of the aortic sinus in an apoE-deficient mouse model of atherosclerosis.

The ability of the compounds of this invention to block the migration of monocytes and prevent or ameliorate inflammation, which is demonstrated in the specific examples, indicates their usefulness in the treatment and management of disease states associated with aberrant leukocyte recruitment.

The use of the compounds of the invention for treating inflammatory and autoimmune disease by combination therapy may also comprise the administration of the compound of the invention to a mammal in combination with common anti-inflammatory drugs, cytokines, or immunomodulators.

The compounds of this invention are thus used to inhibit leukocyte migration in patients which require such treatment. The method of treatment comprises the administration, orally or parenterally, of an effective quantity of the chosen compound of the invention, preferably dispersed in a pharmaceutical carrier. Dosage units of the active ingredient are generally selected from the range of 0.01 to 1000 mg/kg, preferably 0.01 to 100 mg/kg, and more preferably 0.1 to 50 mg/kg, but the range will be readily determined by one skilled in the art depending on the route of administration, age, and condition of the patient. These dosage units may be administered one to ten times daily for acute or chronic disease. No unacceptable toxicological effects are expected when compounds of the invention are used in accordance with the present invention.

The invention compounds may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like, or may be administered orally. Formulations may optionally be liposomal formulations, emulsions, formulations designed to administer the drug across mucosal membranes or transdermal formulations. Suitable formulations for each of these methods of administration may be found in, for example, A. Gennaro, ed., Remington: The Science and Practice of Pharmacy, 20th ed., Lippincott, Williams & Wilkins, Philadelphia, Pa.

EXAMPLES

The following Examples serve to illustrate the preparation, properties, and therapeutic applications of the compounds of this invention. These Examples are not intended to limit the scope of this invention, but rather to show how to synthesize and use the compounds of this invention.

Preparation of the Compounds of the Invention: General Procedures

The following general procedures may be employed for the preparation of the compounds of the present invention.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as Fieser and Fieser's Reagents for Organic Synthesis, vols. 1–17, John Wiley and Sons, New York, N.Y., 1991; Rodd's Chemistry of Carbon Compounds, vols. 1–5 and supps., Elsevier Science Publishers, 1989; Organic Reactions, vols. 1–40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

In some cases, protective groups may be introduced and finally removed. For example, suitable protective groups for amino, hydroxy, and carboxy groups are described in Greene et al., Protective Groups in Organic Synthesis, 2nd ed., John Wiley and Sons, New York, 1991. Activation of carboxylic acids can be achieved by using a number of different reagents as described in Larock, Comprehensive Organic Transformations, VCH Publishers, New York, 1989.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Generally, a compound of Formula I, II, or III:

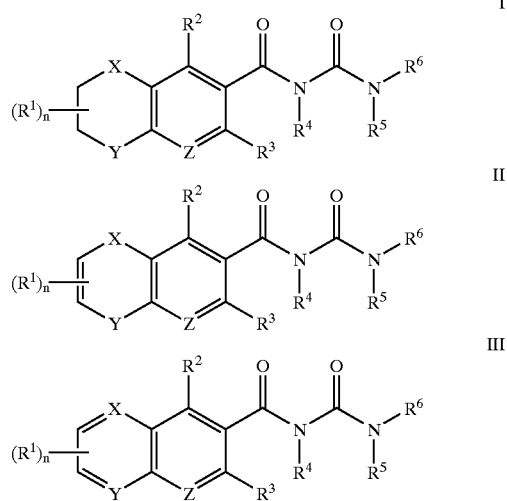

wherein X, Y, Z, and $R^1$-$R^6$ are as defined in the Summary of the Invention, may be prepared by a process comprising-said process comprising:

(a) contacting a compound of Formula Ib, IIb, or IIIb

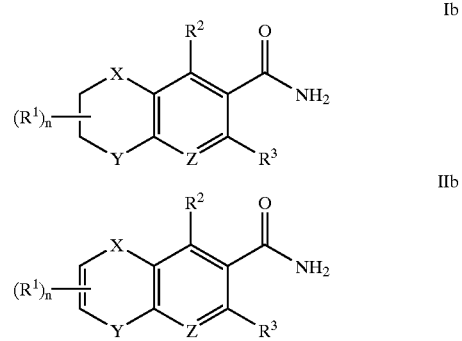

-continued

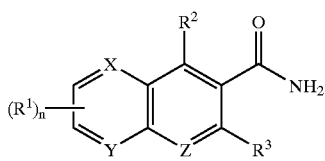

IIIb wherein X, Y, Z, and $R^1$-$R^3$ are as defined above,
with a compound of the formula $R^6$—N=C=O
where $R^6$ is as defined above,
under appropriate conditions,
to produce a compound of Formula I, II, or III, wherein $R^4$ and $R^5$ are both H; or (b) contacting a compound of Formula Ib, IIb or IIIb above with a haloformylation reagent and a compound of the formula

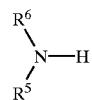

where $R^5$ and $R^6$ are as defined above,
under appropriate conditions,
to produce a compound of Formula I, II or III, wherein $R^4$ is H; or (c) elaborating substituents of a compound of Formula I, II or III in a manner known per se; or (d) reacting the free base of a compound of Formula I, II or III with an acid to give a pharmaceutically acceptable addition salt; or (e) reacting an acid addition salt of a compound of Formula I, II or III with a base to form the corresponding free base; or (f) converting a salt of a compound of Formula I, II, or III to another pharmaceutically acceptable salt of a compound of Formula I, II, or III; or (g) resolving a racemic mixture of any proportions of a compound of Formula I, II, or III to yield a stereoisomer thereof.

Step (a) may carried out in the presence of an organic solvent or a mixture of solvents at elevated temperatures, and the organic solvent may be toluene and the reaction may be carried out under refluxing conditions.

Step (b) may be carried out in an organic solvent or a mixture of solvents at elevated temperatures. The haloformylation reagent may be a compound of the formula A—(CO)—B wherein A and B are, independently, suitable leaving groups such as halogens, —COCl, —COBr and the like. The haloformylation reagent and organic solvent employed in step (b) may be oxalyl chloride and THF, respectively, and the reaction may be heated to above 50° C.

The compounds of the invention can be synthesized as shown in the following examples. These examples are merely illustrative of some methods by which the compounds of this invention can be synthesized, and various modifications to these examples can be made and will be suggested to a person of ordinary skill in the art having regard to this disclosure.

Procedure A:

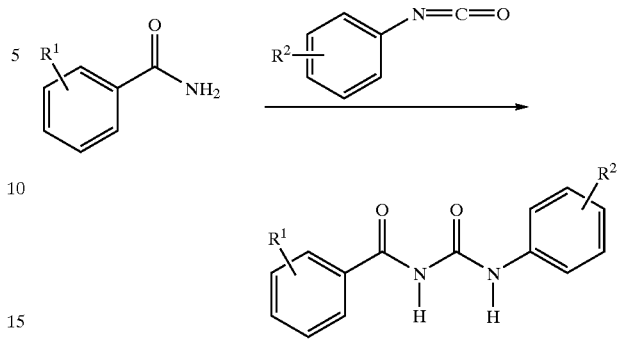

Compounds of the present invention may be prepared starting with a carboxamide and an isocyanate. Carboxamides and isocyanates starting materials may be purchased from various different commercial sources, such as, for example, the Aldrich Chemical Company, supra, or they may be prepared from standard procedures known in the art for preparing these compounds, such as the procedures described in the above cited references. The isocyanates may also be prepared according to the procedures described in the examples below. Typically, an aryl carboxamide is treated with an aryl isocyanate in an organic solvent or mixtures of suitable organic solvents. Preferably, the organic solvent is toluene. The carboxamide and the isocyanate may be combined as solutions or suspensions, depending on the solubilities of the compounds in the selected solvent. The carboxamide and the isocyanate may be added in a stoichiometric ratio (1:1), or a slight excess of the isocyanate may be used, for example between 1.01 fold and 2 fold excess, but typically about 1.01 to about 1.2 fold excess. Typically, the isocyanate is added to a suspension of the carboxamide in toluene, and the resulting mixture is heated until the reaction is determined to be complete. The reaction mixture may be heated at about 10° C. to about 150° C., preferably at about 40° C. to about 120° C. under an inert atmosphere such as nitrogen, or the reaction mixture may be maintained at the refluxing temperature of the mixture. The reaction may be allowed to proceed to completion in about 10 minutes to 24 hours. Preferably, the reaction is heated to reflux until the reaction is complete, over about 6 to 24 hours.

Upon cooling of the reaction mixture, the resulting product may be isolated by conventional techniques. Typically, the product is isolated by filtration. The precipitated solid may be filtered, washed with a solvent or a series of solvents, and isolated without further purification. Preferably, the precipitated product may be washed with a combination of toluene, methanol and then with ether, and the product may be dried under vacuum. If desired, the product may be further purified using conventional techniques, such as by recrystallization, chromatography, etc.

Procedure B:

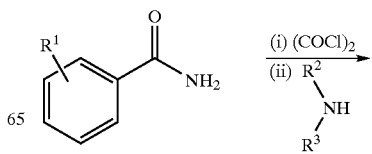

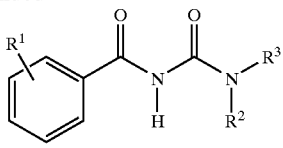

The compounds of the present invention may also be prepared from the condensation of an isocyanate with an amine. The isocyanate may be prepared from the corresponding carboxamide or may be obtained from commercial sources. Depending on the desired substitution of the amine, optionally, the amine may be substituted with an amine protecting group, such that the protecting group may be removed in a subsequent step if desired. In the first step of the process, a carboxamide in a suitable aprotic solvent is treated with a carbonylation reagent to form the corresponding isocyanate derivative. Typically, the aprotic solvent is dichloromethane, toluene, 2-methyltetrahydrofuran or THF, and them carbonylation reagent is oxalyl chloride. Preferably, the aprotic solvent is dichloromethane. Oxalyl chloride is preferably present in an excess, for example, between 1.1 to 3.0 equivalents, typically about 1.5 equivalents, over the carboxamide. The reaction is generally performed under an inert atmosphere where the mixture is heated to 50° C. to 175° C. for 15 minutes to 24 hours or until the reaction is deemed complete. Typically, the reaction is heated to reflux over 2 to 16 hours under nitrogen, and then cooled to room temperature. The solvent is removed in vacuo by distillation, and the resulting isocyanate is then condensed with a primary or secondary amine. Condensation with the amine may be performed by the addition of a solution of the amine in an aprotic solvent, such as THF, under an inert atmosphere, at a temperature between 0° C. and 20° C., preferably between 0° C. and 5° C. If the carbonylation and the subsequent condensation reaction are performed in the same solvent, the solvent removal step may be eliminated. Preferably, the reaction is performed at 0° C. to 5° C. for 1 to 24 hours, or until the reaction is complete. The solvent is removed by concentration under reduced pressure, and the product is isolated by conventional techniques such as filtration and washing of the crude product with a solvent followed by drying under vacuum, recrystallization, etc.

Procedure C:

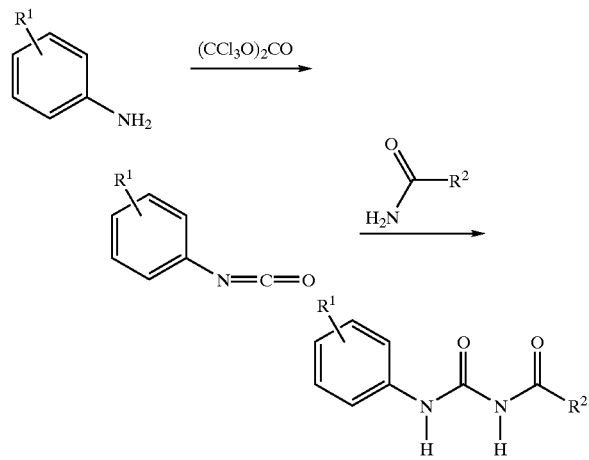

The preparation of the compounds of the present invention may also be performed by condensation of an amine or aniline derivative with a phosgene equivalent, followed by reaction of the resulting isocyanate with a carboxamide. Typically, a solution of an aniline or aniline derivative and triphosgene in tetrachloroethane or other suitable organic solvent is combined and stirred at 25° C. to 80° C. under an inert atmosphere for 2 to 12 hours or until the reaction is complete as determined by TLC or HPLC analysis of the reaction mixture. The solvent is removed under reduced pressure and the residue is dissolved in an aprotic solvent, such as toluene, and the resulting mixture is treated with a carboxamide. The mixture is heated to about 50° C. to 150° C., preferably from about 75° C. to 115° C. More preferably, the reaction mixture is heated to reflux for 2 to 24 hours or until the reaction is complete, and allowed to cool to room temperature. The precipitated solid is isolated by conventional techniques such as filtration. The filtered solid is then washed with a suitable solvent or mixtures of solvents. Typically, the solid is washed with toluene, methanol and then ether, and the washed product is dried in vacuo to give the product.

Procedure D:

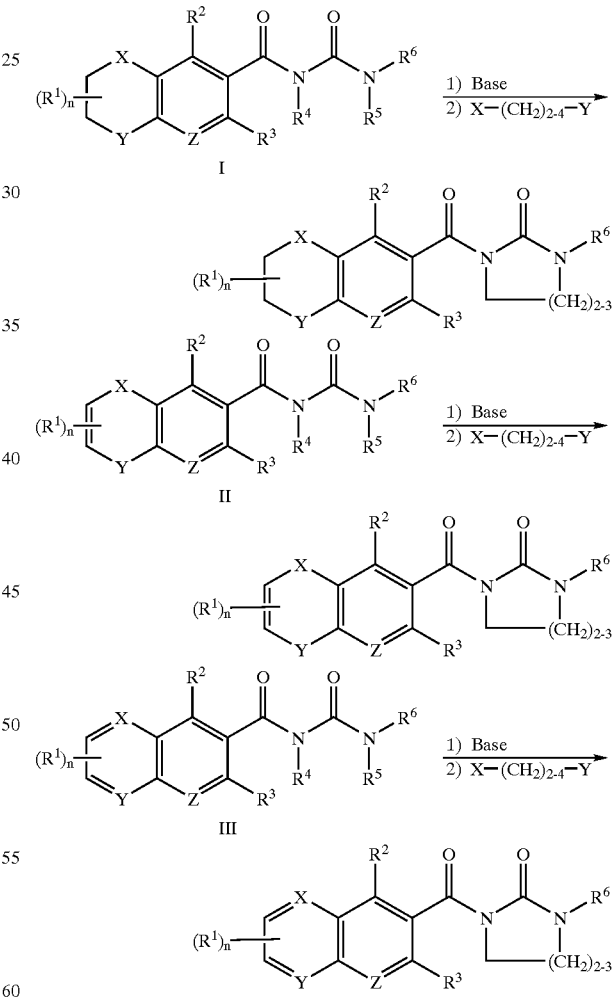

Cyclic acyl ureas of the present invention may be prepared according to methods known in the art. One method comprises the alkylation of the acyl urea nitrogens with an alkylating agent generically represented above as $X-(CH_2)_{2-4}-Y$, where X and Y are leaving groups, and may be the same or different. Leaving groups known in the art include halides, methanesulfonates, trifluoromethanesulfonates, p-toluenesulfonates, p-bromotoluenesulfonate, p-nitrobenzenesulfonates and the like. Representative alkylating agents include 1,2-dibromoethane, 1,3-dibromoethane, 1,3-dibromopropane, and the corresponding sulfonates and mixed halosulfonates. Typically, the acyl urea is treated with a base in an organic solvent or mixtures of solvents. Preferably, the base is an inorganic base such as sodium hydride, or an organic base such as dimethyl sulfoxide and sodium hydride. Preferably, the solvent is a polar, aprotic solvent such as tetrahydrofuran, dimethylformamide, dimethyl sulfoxide, glycols, or mixtures of such solvents. Typically, a solution or suspension of the acyl urea is slowly added to the base in an organic solvent at about 0° C. to about 25° C., and the resulting mixture is stirred for about 10 minutes to about 5 hours, preferably about 30 minutes. The alkylating agent is added and the mixture is stirred until the reaction is deemed complete. Alkylation of both urea nitrogens may be accomplished in a single step, or may be accomplished sequentially in a two step procedure be exposing the partially alkylated product with the same or different base. The reaction is then quenched with a solvent, preferably water, and the mixture is extracted multiple times with an organic solvent. Preferably, the extracting solvent is dichloromethane. The combined organic extracts are washed with water, dried over anhydrous magnesium sulfate and concentrated under reduced pressure to afford the product, which may be purified using standard conditions known in the art. Purification may be performed by silica gel chromatography in a mixture of organic solvents, such as ethyl acetate and petroleum ether.

Example 1

2H,3H-Benzo[3,4-e]1,4-dioxin-6-yl-N-{[(3-iodophenyl)amino]carbonyl}-carboxaminde (10)

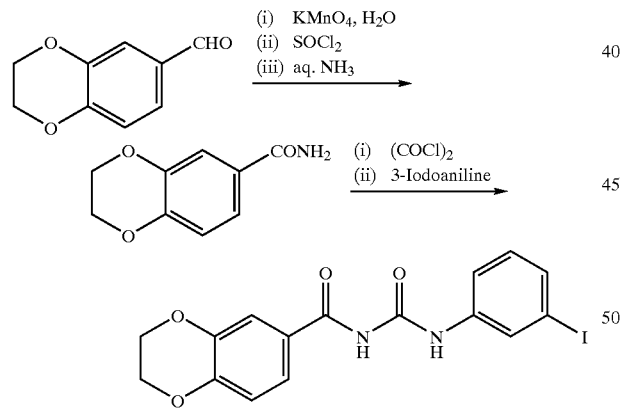

A solution of potassium permanganate (3.31 g) in water (100 mL) was added over 30 min to a stirred solution of 1,4-benzodioxan-6-carboxaldehyde (2.50 g) in water (40 mL) at 90° C. Stirring was continued at 90° C. for an additional 45 min and the mixture was then cooled to ambient temperature. The mixture was made basic (pH 10) with aqueous 1M KOH solution, filtered, and the filtrate was cooled in an ice-bath and acidified to pH 3 with concentrated HCl. The precipitated solid was collected by filtration, washed with water, and dried. The solid was dissolved in dichloromethane, washed with saturated sodium chloride solution, and dried over magnesium sulfate. The solvent was evaporated under reduced pressure to furnish 2H,3H-benzo[e]1,4-dioxane-6-carboxylic acid as a white powder. A portion of this material (1.05 g) was dissolved in thionyl chloride (10 mL) and the mixture heated at 50° C. under a nitrogen atmosphere for 7 h. After cooling to room temperature, the excess thionyl chloride was removed under reduced pressure and the residue dried under high vacuum for 1 h. The solid was cooled in an ice-bath and treated with ammonium hydroxide solution (10 mL, 28–30% ammonia). The mixture was stirred at 0° C. for 5 min, and at room temperature for an additional 1 hr. The product was collected by filtration, washed with water and dried under high vacuum to provide 2H,3H-benzo[e]1,4-dioxane-6-carboxamide as a white powder. A portion of this material (0.90 g) was suspended in anhydrous dichloromethane under nitrogen and treated with oxalyl chloride (3.8 mL of a 2M solution in dichloromethane). The mixture was heated at reflux for 15 h, cooled to room temperature, and concentrated under reduced pressure. The residue was dissolved in anhydrous tetrahydrofuran (10 mL), cooled in an ice-bath, and treated with 3-iodoaniline (604 μL). The ice-bath was removed and the reaction mixture was stirred at ambient temperature for 45 min. The resulting solid was filtered, washed with dichloromethane and methanol, and dried under high vacuum to produce the title compound as a white powder.

$^1$H NMR (DMSO-$d_6$) δ 4.29–4.32 (m, 4H), 6.90 (d, 1H, J=8.3 Hz), 7.14 (t, 1H, J=7.9 Hz), 7.45 (d, 1H, J=7.9 Hz), 7.50 (d, 1H, J=6.8 Hz), 7.58–7.61 (m, 2H), 8.10 (s, 1H), 10.88 (s, 2H). MS (ESI) m/z 423.

Example 2

N-{[(3-phenylphenyl)amino]carbonyl}quinoxalin-6-ylcarboxamide (78)

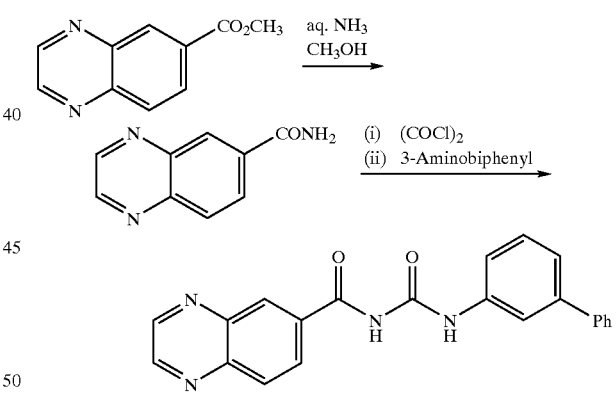

A suspension of methyl quinoxaline-6-carboxylate (2.00 g) in methanol (7.0 mL) and 28–30% ammonia (14 mL) was stirred in a sealed tube at room temperature for 16 h. The precipitated solid was filtered, washed with water and dried under high vacuum to give quinoxaline-6-carboxamide as a white powder. A portion of this material (0.10 g) was suspended in anhydrous dichloromethane and treated with oxalyl chloride (1.0 mL of a 2M solution in dichloromethane) under a nitrogen atmosphere. The mixture was heated at reflux for 16 h and concentrated under reduced pressure. The residue was dissolved in anhydrous tetrahydrofuran (1 mL) and added to an ice-cooled solution of 3-aminobiphenyl (0.98 g) in anhydrous tetrahydrofuran (1 mL). The mixture was stirred at room temperature for 2 h. The solvent was evaporated and the residue taken up in methanol and filtered to give N-{[(3-phenylphenyl)-amino]carbonyl}quinoxalin-6-ylcarboxamide as a white powder.

$^1$H NMR (DMSO-$d_6$) δ 7.37–7.47 (m, 3H), 7.50 (t, J=7.2 Hz, 2H), 7.65 (d, J=7.8 Hz, 1H), 7.69 (d, J=7.2 Hz, 2H) 7.91 (s, 1H), 8.25 (d, J=8.8 Hz, 1H), 8.37 (dd, J=8.8, 1.9 Hz, 1H), J=1.9 Hz, 1H), 9.09 (s, 2H), 10.85 (s, 1H), 11.44 (s, 1H). MS (ESI) m/z 369.

Example 3

N-{[(3-chlorophenyl)amino]carbonyl}-1,2,3,4-tetrahydroquinoxalin-6-yl-carboxamide (115)

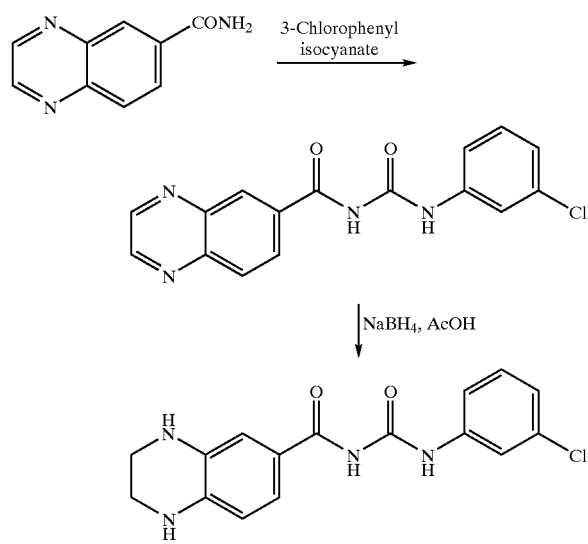

Quinoxaline-6-carboxamide (0.10 g) was dissolved in hot toluene (30 mL) and azeotroped for 1 h. The solution was cooled to room temperature and treated with 3-chlorophenyl isocyanate (0.133 g). The mixture was heated at reflux for 16 h and then cooled to room temperature. The precipitated solid was filtered, washed with methanol, and dried under high vacuum to give N-{[(3-chlorophertyl)amino]carbonyl}quinoxalin-6-ylcarboxamide as a white solid. A portion of this material (40 mg) was suspended in acetic acid (1.5 mL) in an ice-water bath, and the suspension treated with sodium borohydride (9 mg). After TLC showed complete consumption of the starting material, the solution was poured into water (20 mL). The precipitated solid was filtered, washed with water, and dried under high vacuum to give N-{[(3-chlorophenyl)amino]carbonyl}-1,2,3,4-tetrahydroquinoxalin-6-ylcarboxamide as a yellow solid.

$^1$H NMR (DMSO-$d_6$) δ 3.18 (br s, 2H), 3.32 (br s, 2H), 5.56 (br s, 1H), 6.37 (d, J=8.3 Hz, 1H), 6.38 (br s, 1H), 7.09 (d, J=1.9 Hz, 1H), 7.13 (dd, J=7.8, 1.9 Hz, 1H), 7.26 (dd, J=8.3, 1.9 Hz, 1H), 7.35 (t, J=7.8 Hz, 1H), 7.41 (dd, J=7.8, 1.9 Hz, 1H), 7.82 (t, J=1.9 Hz, 1H), 10.39 (s, 1H), 11.25 (s, 1H). MS (ESI) m/z 331.

Example 4

N-{[(3,4-dichlorophenyl)amino]carbonyl}(4-methyl (2H,3H-benzo[3,4-e]-1,4-oxazaperhydroin-6-yl))carboxamide (141)

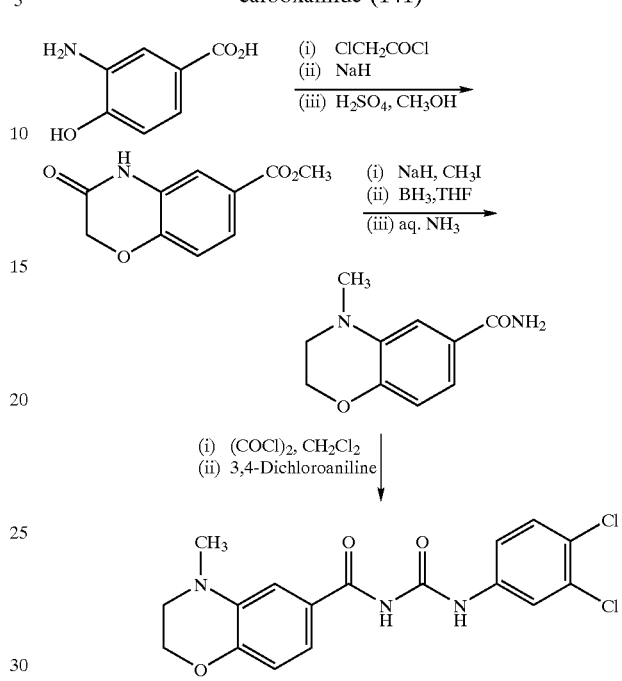

Chloroacetyl chloride (2.23 g) was added dropwise to a stirred suspension of 3-amino-4-hydroxybenzoic acid (3.00 g) in anhydrous dichloromethane kept at −60° C. under a nitrogen atmosphere. The cooling bath was removed and the mixture was stirred at room temperature for 16 h. Pyridine (9 mL) was added and the precipitated solid was collected by filtration, washed with methanol, and dried under high vacuum. A portion of this material (3.00 g) was suspended in anhydrous tetrahydrofuran (150 mL), cooled to −60° C. (dry ice/acetone) and treated with sodium hydride (2.10 g of a 60% suspension in mineral oil) under a nitrogen atmosphere. The cooling bath was removed and the mixture was stirred at room temperature for 16 h, quenched with methanol, and concentrated under reduced pressure. The residue was dissolved in water and acidified to pH 1 with concentrated HCl. The resulting precipitate was filtered, washed with water, and dried under high vacuum to give 3-oxo-2H,4H-benzo[e]-1,4-oxazaperhydroine-6-carboxylic acid. To a suspension of this material (2.80 g) in methanol (84 mL) was added sulfuric acid (0.5 mL) and the mixture was heated at reflux for 16 h. The solvent was removed under reduce pressure and the residue was resuspended in methanol and filtered to give methyl 3-oxo-2H,4H-benzo[3,4-e]-1,4-oxazaperhydroine-6-carboxylate. A suspension of this material (1.50 g) in anhydrous tetrahydrofuran (50 mL) was cooled to 0° C. and treated with sodium hydride (0.87 g of a 60% suspension in mineral oil). The suspension was stirred for 1 h and treated with iodomethane (3.08 g). The cooling bath was removed and the mixture was stirred at room temperature for 16 h, and quenched with methanol. The solvent was removed under reduce pressure, and the residue was suspended in water, filtered, washed with water, and dried under high vacuum to afford methyl 4-methyl-3-oxo-2H-benzo[3,4-e]-1,4-oxazaperhydroine-6-carboxylate. A portion of this material (1.00 g) was dissolved in anhydrous tetrahydrofuran (50 mL) under nitrogen and treated with borane-tetrahydrofuran complex (7.5 mL of a 1M solution in tetrahydrofuran). The mixture was heated at reflux for 1 h, cooled to room temperature, and quenched by addition of methanol. The solvent was evaporated under reduce pressure and the residue was suspended in saturated sodium bicarbonate solution and extracted with dichloromethane. Concentration of the organic extract yielded methyl 4-methyl-2 2H,3H-benzo[3,4-e]1,4-oxazaperhydroine-6-carboxylate as a yellow oil. This material was dissolved in methanol (15 mL) and treated with 28–30% ammonia (30 mL). The mixture was stirred at room temperature for 16 h, and then treated with 5N NaOH solution. The precipitated solid was collected by filtration to give 4-methyl-2H,3H-benzo[e]-1,4-oxazaperhydroine-6-carboxamide as a white solid. A portion of this material (25 mg) was suspended in anhydrous dichloromethane (2.5 mL), and treated with oxalyl chloride (0.2 mL of a 2M solution in dichloromethane). The suspension was heated at reflux for 16 h and concentrated under reduced pressure. The residue was resuspended in anhydrous THF (0.5 mL) and added to an ice-cooled solution of 3,4-dichloroaniline (21 mg) in anhydrous tetrahydrofuran (1 mL). The mixture was stirred for 1 h and concentrated under reduced pressure. The residue was suspended in methanol, filtered, and washed with ether to give N-{[(3,4-dichlorophenyl)amino]carbonyl}(4-methyl-(2H,3H-benzo[3,4-e]-1,4-oxazaperhydroin-6-yl)) carboxamide as a white powder.

¹H NMR (DMSO-d₆) δ 2.91 (s, 3H), 3.28 (t, J=4.1 Hz, 2H), 4.31 (t, J=4.1 Hz, 2H), 6.78(d, J=8.2 Hz, 1H), 7.37(d, J=8.2 Hz, 1H), 7.39 (s, 1H), 7.53 (dd, J=6.6, 2.2 Hz, 1H), 7.56(d, J=6.6 Hz, 1H), 8.02 (d, J=2.2 Hz, 1H), 10.94(s, 1H), 11.13 (s, 1H). MS (ESI) m/z 378.

Example 5

N-{[(3-bromophenyl)amino]carbonyl}(4-methyl(2H, 3H-benzo[e]-1,4-oxaza-perhydroin-7-yl)) carboxamide (144)

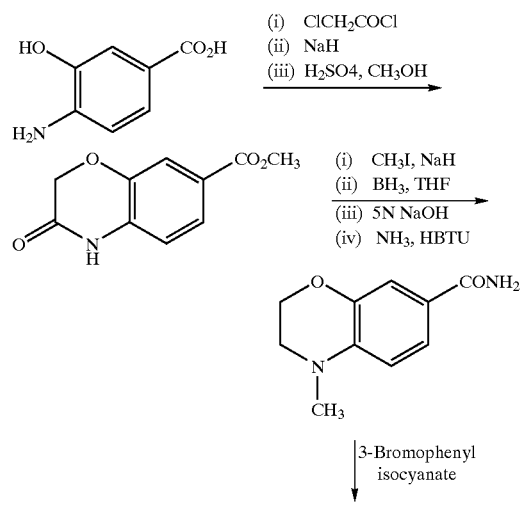

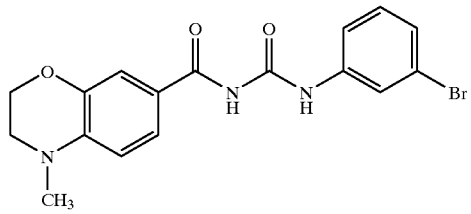

4-Amino-3-hydroxybenzoic acid (5.00 g) was suspended in dichloromethane (200 mL) under a nitrogen atmosphere and cooled to −60° C. Chloroacetyl chloride (3.72 g) was added dropwise, and the mixture was allowed to warm up to room temperature and stirred at this temperature for 16 h. Pyridine (15 mL) was added and the precipitated solid was filtered, washed with methanol, and dried under high vacuum to yield pyridinium 4-(2-chloroacetylamino)-3-hydroxybenzoate. A portion of this material (8.00 g) was suspended in anhydrous tetrahydrofuran (25 mL) under a nitrogen atmosphere and cooled to −60° C. Sodium hydride (4.15 g of a 60% suspension in mineral oil) was added, the cooling bath was removed, and the mixture was stirred at room temperature for 16 h. It was then cooled to 0° C., quenched by addition of methanol, and concentrated under reduced pressure. The residue was suspended in water and acidified to pH 1 with concentrated hydrochloric acid. The precipitated solid was filtered, washed with water, and dried under high vacuum to give 3-oxo-2H,4H-benzo[e]-1,4-oxazaperhydroine-7-carboxylic acid. A portion of this material (3.50 g) was suspended in methanol (115 mL) and treated with sulfuric acid (0.887 g). The mixture was heated at reflux for 16 h and cooled to room temperature. The precipitated solid was filtered, washed with methanol, and dried to give methyl 3-oxo-2H,4H-benzo[e]1,4-oxazaperhydroine-7-carboxylate. A portion of this material (2.00 g) was suspended in anhydrous tetrahydrofuran (100 mL), cooled to 0° C., and treated with sodium hydride(0.77 g of a 60% suspension in mineral oil). The suspension was stirred for 1 h, treated with iodomethane (2.74 g), and the mixture stirred at room temperature for 16 h. The solvent was evaporated and the residue was suspended in ammonium chloride solution, filtered, washed with water, and dried under high vacuum to give methyl 4-methyl-3-oxo-2H-benzo[e]-1,4-oxazaperhydroine-7-carboxylate. A portion of this material (1.89 g) was suspended in tetrahydrofuran (100 mL) and treated with a 1M solution of borane-tetrahydrofuran complex in tetrahydrofuran (14.2 mL). The mixture was heated at reflux for 4 h and cooled to room temperature. The solvents were removed under reduced pressure and the residue was purified by column chromatography eluting with n-hexane/ethyl acetate to afford methyl 4-methyl-2H,3H-benzo[e]-1,4-oxazaperhydroine-7-carboxylate as a yellow solid. A portion of this material (0.53 g) was dissolved in methanol (5 mL) and 5N NaOH solution (2.55 mL) and the mixture was heated at reflux for 4 h. After cooling to room temperature, the mixture was diluted with water and acidified to pH 2 with concentrated hydrochloric acid. The precipitated solid was filtered, washed with water, and dried under high vacuum to give 4-methyl-2H,3H-benzo[e]-1,4-oxazaperhydroine-7-carboxylic acid as a white solid. A portion of this material (0.40 g) was suspended in a 0.5M solution of ammonia in dioxane (10.4 mL), and the suspension treated with diisopropylethylamine (1.34 g), O-(benzotriazol-1-yl)-N,N,N',N'-tetramethyluronium hexafluorophosphate (0.86 g) and DMF (5 mL). The mixture was stirred at room temperature for 16 h. The solvent was removed under reduce pressure, and the residue was purified by column chromatography eluting with dichloromethane/methanol to yield 4-methyl-2H,3H-benzo[e]-1,4-oxazaperhydroine-7-carboxamide. A portion of this material (0.10 g) was dissolved in hot toluene (30 mL) and azeotroped for 1 h. The solution was cooled to room temperature and treated with 3-bromophenyl isocyanate (0.226 g). The mixture was heated at reflux for 16 h, cooled to room temperature, and the precipitated solid was collected by filtration, washed with methanol and dichloromethane, and dried under high vacuum to yield N-{[(3-bromophenyl) amino]carbonyl}(4-methyl(2H,3H-benzo[e]-1,4-oxazaperhydroin-7-yl))-carboxamide as a white solid.

$^1$H NMR(DMSO-d6) δ2.96 (s, 3H), 3.39 (t, J=4.2 Hz, 2H), 4.22 (m, 2H), 6.73 (d, J=8.6 Hz, 1H), 7.24–7.36 (m, 2H), 7.42 (d, J=1.9 Hz, 1H), 7.47 (m, 1H), 7.64 (dd, J=8.6, 1.9 Hz), 7.98 (s, 1H), 10.68 (s, 1H), 11.16 (s, 1H). MS (ESI) m/z 388, 390.

Compounds of the Invention

The compounds shown in Tables 1–10 were prepared either by the procedures described above or by modifications of these procedures familiar to those skilled in the art.

TABLE 1

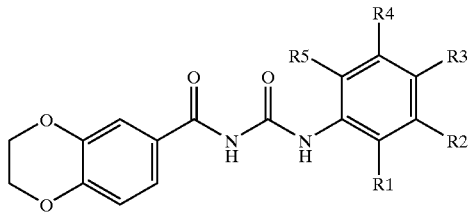

| Compound | R1 | R2 | R3 | R4 | R5 | MW | MS (m/z) |
|---|---|---|---|---|---|---|---|
| 1 | H | Cl | H | H | H | 332.74 | 331, 333 |
| 2 | H | Cl | Cl | H | H | 367.19 | 365, 367, 369 |
| 3 | H | Cl | OH | H | H | 348.74 | 347, 349 |
| 4 | H | H | CF$_3$ | H | H | 366.29 | 365 |
| 5 | H | H | Cl | H | H | 332.74 | 331, 333 |
| 6 | H | Br | H | H | H | 377.19 | 375, 377 |
| 7 | H | CN | H | H | H | 323.31 | 322 |
| 8 | Cl | H | Cl | H | H | 367.18 | 365, 367, 369 |
| 9 | H | H | I | H | H | 424.19 | 423 |
| 10 | H | I | H | H | H | 424.19 | 423 |
| 11 | H | OCF$_3$ | H | H | H | 382.29 | 381 |
| 12 | H | i-Pr | H | H | H | 340.38 | 339 |
| 13 | H | Me | H | H | H | 312.32 | 311 |
| 14 | I | H | H | H | H | 424.19 | 423 |
| 15 | H | CF$_3$ | H | H | H | 366.29 | 365 |
| 16 | H | SCF$_3$ | H | H | H | 398.36 | 397 |
| 17 | H | Et | H | H | H | 326.35 | 325 |
| 18 | H | OEt | H | H | H | 342.35 | 341 |
| 19 | H | Oi-Pr | H | H | H | 356.38 | 355 |
| 20 | H | Ph | H | H | H | 374.39 | 373 |
| 21 | H | t-Bu | H | H | H | 354.40 | 353 |
| 22 | H | Cl | Me | H | H | 346.79 | 345, 347 |
| 23 | H | I | Me | H | H | 438.21 | 437 |
| 24 | H | CF$_3$ | Me | H | H | 380.32 | 379 |
| 25 | H | CF$_3$ | F | H | H | 384.28 | 383 |
| 26 | H | CF$_3$ | CF$_3$ | H | H | 434.29 | 433 |
| 27 | H | CF$_3$ | H | CF$_3$ | H | 434.29 | 433 |
| 28 | H | CF$_3$ | Cl | H | H | 400.74 | 399, 401 |
| 29 | H | OPh | H | H | H | 390.39 | 389 |
| 30 | H | NO$_2$ | H | H | H | 343.29 | 342 |
| 31 | H | Cl | H | Cl | H | 367.19 | 365, 367, 369 |
| 32 | H | Ac | H | H | H | 340.33 | 339 |
| 33 | H | CO$_2$Me | H | H | H | 356.33 | 355 |
| 34 | H | 1H-1,2,3,4-tetrazol-5-yl | H | H | H | 366.34 | 365 |
| 35 | H | ethynyl | H | H | H | 322.32 | 321 |
| 36 | Me | Cl | H | H | H | 346.77 | 345, 347 |
| 37 | Me | H | H | Cl | H | 346.77 | 345, 347 |
| 38 | Me | H | H | I | H | 438.22 | 437 |
| 39 | OMe | H | H | Cl | H | 362.77 | 361, 363 |
| 40 | Et | Cl | H | H | Et | 388.85 | 387, 389 |
| 41 | H | 1,3-thiazol-2-yl | H | H | H | 381.41 | 382 |
| 42 | H | 2-thienyl | H | H | H | 380.42 | 381 |
| 42 | H | 3-thienyl | H | H | H | 380.42 | 379 |
| 44 | H | 2-furfuryl | H | H | H | 364.56 | 363 |
| 45 | H | 2-pyridyl | H | H | H | 375.38 | 374 |
| 46 | H | H | 1H-1,2,3,4-tetrazol-5-yl | H | H | 366.34 | 365 |
| 47 | H | CO$_2$Me | Br | H | H | 435.22 | 435 |
| 48 | H | CF$_3$ | H | CO$_2$H | H | 410.30 | 409 |

TABLE 1-continued

| Compound | R1 | R2 | R3 | R4 | R5 | MW | MS (m/z) |
|---|---|---|---|---|---|---|---|
| 49 | H | CF$_3$ | H | OH | H | 382.29 | 381 |
| 50 | H | CO$_2$H | Br | H | H | 412.20 | 419 |
| 51 | H | Cl | OC(O)CH$_3$ | H | H | 390.77 | 389, 391 |
| 52 | H | Cl | OC(O)CH$_2$CO$_2$CH$_3$ | H | H | 448.81 | 447, 449 |
| 53 | H | Cl | OC(O)CH$_2$CO$_2$H | H | H | 434.78 | 433, 435 |
| 54 | H | Cl | OCH$_2$CO$_2$CH$_3$ | H | H | 420.80 | 419, 421 |
| 55 | H | Cl | OCH$_2$CO$_2$H | H | H | 406.77 | 405 |
| 56 | H | Cl | OCH$_2$CO$_2$CH$_2$Ph | H | H | 496.90 | 495, 497 |
| 57 | H | Cl | CO$_2$Na | H | H | 398.03 | ND |
| 58 | H | CO$_2$H | Cl | H | H | 376.75 | 375, 377 |
| 59 | H | H | CO$_2$Na | H | H | 364.28 | ND |
| 60 | H | CO$_2$Na | H | H | H | 364.28 | ND |

TABLE 2

| Compound | R | MW | MS (m/z) |
|---|---|---|---|
| 61 | 2-chloro-4-(pyridyl) | 333.73 | 333, 334 |
| 62 | 6-chloro-4-methylpyrimidin-2-yl | 348.74 | 332, 334 |
| 63 | 5-(trifluoromethyl)(1,3,4-thiadiazol-2-yl) | 374.30 | 373 |

TABLE 3

| Compound | R1 | R2 | MW | MS (m/z) |
|---|---|---|---|---|
| 64 | CH$_2$OCH$_3$ | CH$_2$OCH$_3$ | 420.84 | 421, 423 |
| 65 | CH$_2$OCH$_2$CH$_2$OCH$_3$ | H | 420.84 | 421, 423 |

TABLE 4

| Compound | R1 | R2 | R3 | R4 | R5 | MW | MS (m/z) |
|---|---|---|---|---|---|---|---|
| 66 | H | Cl | H | H | H | 326.74 | 325, 327 |
| 67 | H | Br | H | H | H | 371.19 | 369, 371 |
| 68 | H | H | CF$_3$ | H | H | 360.29 | 359 |
| 69 | H | CF$_3$ | H | H | H | 360.29 | 359 |
| 70 | H | OCF$_3$ | H | H | H | 376.29 | 375 |
| 71 | H | i-Pr | H | H | H | 334.38 | 333 |
| 72 | H | I | H | F | H | 418.19 | 417 |
| 73 | H | CF$_3$ | F | H | H | 378.28 | 379 |
| 74 | H | Cl | OH | H | H | 342.74 | 343, 345 |
| 75 | H | CF$_3$ | Cl | H | H | 394.74 | 395 |
| 76 | H | CN | H | H | H | 317.31 | 318 |
| 77 | Cl | H | Cl | H | H | 361.19 | 361, 363 |
| 78 | H | Ph | H | H | H | 368.39 | 369 |

TABLE 4-continued

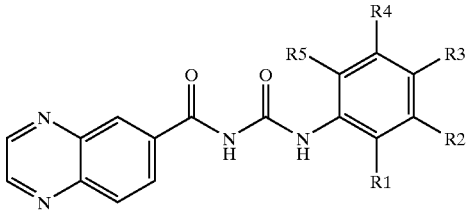

| Compound | R1 | R2 | R3 | R4 | R5 | MW | MS (m/z) |
|---|---|---|---|---|---|---|---|
| 79 | H | Oi-Pr | H | H | H | 350.38 | 351 |
| 80 | H | OPh | H | H | H | 384.39 | 385 |
| 81 | H | CF₃ | H | CF3 | H | 428.29 | 429 |
| 82 | H | Cl | Cl | H | H | 361.87 | 359, 361, 363 |
| 83 | H | CO₂Me | Cl | H | H | 384.78 | 383, 385 |
| 84 | H | CO₂Et | Cl | H | H | 398.80 | 397 |
| 85 | H | CO₂Na | Cl | H | H | 392.73 | 369, 371 |
| 86 | H | H | CO₂Na | H | H | 358.29 | 335 |
| 87 | H | Cl | OCH₂CO₂Et | H | H | 428.83 | 427 |
| 88 | H | Cl | OCH₂CO₂Na | H | H | 422.76 | 399, 401 |
| 89 | H | CO₂Na | H | H | H | 358.29 | 335 |
| 90 | CO₂Na | Cl | H | H | H | 392.73 | 371 |
| 91 | H | Oi-Pr | CO₂Na | H | H | 416.37 | 393 |
| 92 | H | CO₂Na | H | CF₃ | H | 426.29 | 403 |
| 93 | OH | Cl | H | H | H | 342.74 | 341, 343 |
| 94 | H | OH | CO₂H | H | H | 352.30 | 351 |
| 95 | H | 3-thienyl | H | H | H | 374.42 | 373 |
| 96 | H | 1,3-thiazol-2-yl | H | H | H | 375.54 | 374 |
| 97 | H | 2-furfuryl | H | H | H | 358.36 | 357 |
| 98 | H | Cl | CO₂H | H | H | 370.75 | 369 |
| 99 | H | 2-pyridyl | H | H | H | 369.38 | 368 |
| 100 | H | 2-thienyl | H | H | H | 374.42 | 373 |
| 101 | H | OPh | CO₂H | H | H | 428.40 | 427 |
| 102 | H | benzoyl | H | H | H | 396.40 | 395 |
| 103 | H | CO₂i-Pr | Cl | H | H | 412.83 | 411 |
| 104 | CO₂H | H | Cl | H | H | 370.75 | 369 |
| 105 | H | CF₃ | CO₂Me | H | H | 418.33 | 417 |
| 106 | H | OH | CO₂Me | H | H | 366.33 | 365 |
| 107 | H | Cl | OCH₂CO₂CH₂Ph | H | H | 490.10 | 489, 491 |
| 108 | H | Cl | OCH₂CO₂H | H | H | 400.06 | 399, 401 |

TABLE 5

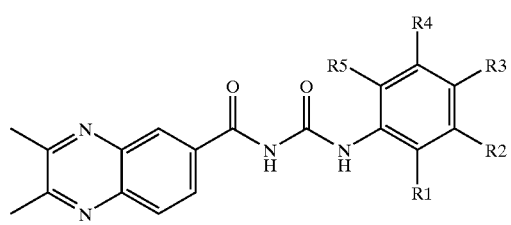

| Compound | R1 | R2 | R3 | R4 | R5 | MW | MS (m/z) |
|---|---|---|---|---|---|---|---|
| 109 | H | Cl | H | H | H | 354.8 | 353, 355 |
| 110 | H | Br | H | H | H | 399.25 | 397, 399 |
| 111 | H | CF₃ | H | H | H | 388.35 | 387 |

TABLE 5-continued

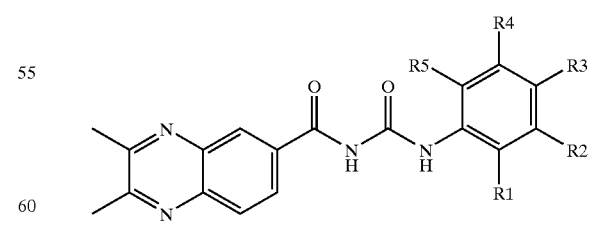

| Compound | R1 | R2 | R3 | R4 | R5 | MW | MS (m/z) |
|---|---|---|---|---|---|---|---|
| 112 | H | Cl | Cl | H | H | 389.24 | 387, 389, 391 |
| 113 | H | CN | H | H | H | 345.36 | 344 |

TABLE 6

| Compound | R1 | R2 | R3 | R4 | R5 | R6 | R7 | MW | MS (m/z) |
|---|---|---|---|---|---|---|---|---|---|
| 114 | H | H | CF$_3$ | H | H | H | H | 364.33 | 363 |
| 115 | H | Cl | H | H | H | H | H | 330.77 | 331, 333 |
| 116 | H | Br | H | H | H | H | H | 375.22 | 375, 377 |
| 117 | H | CF$_3$ | H | H | H | H | H | 364.33 | 365 |
| 118 | H | CF$_3$ | H | H | H | Et | Et | 420.43 | 421 |
| 119 | H | OCF$_3$ | H | H | H | H | H | 380.32 | 381 |
| 120 | H | i-Pr | H | H | H | H | H | 338.41 | 339 |
| 121 | H | I | H | H | H | H | H | 422.22 | 423 |
| 122 | H | CF$_3$ | F | H | H | H | H | 382.32 | 383 |
| 123 | H | CF$_3$ | H | H | H | Me | Me | 392.38 | 393 |
| 124 | H | CF$_3$ | Cl | H | H | H | H | 398.77 | 399, 401 |
| 125 | H | CN | H | H | H | H | H | 321.34 | 322 |
| 126 | H | Ph | H | H | H | H | H | 372.43 | 373 |
| 127 | H | Oi-Pr | H | H | H | H | H | 354.41 | 355 |
| 128 | H | OPh | H | H | H | H | H | 388.43 | 389 |
| 129 | H | CF$_3$ | H | CF$_3$ | H | H | H | 432.32 | 433 |
| 130 | H | Cl | OH | H | H | H | H | 346.77 | 345 |
| 131 | H | CF$_3$ | H | H | H | CH$_2$CH$_2$OH | CH$_2$CH$_2$OH | 452.43 | 453 |
| 132 | H | CF$_3$ | H | H | H | H | CH$_2$CH$_2$OH | 408.38 | 407 |
| 133 | H | Cl | OCH$_2$—CO$_2$Et | H | H | H | H | 432.86 | 431 |
| 134 | H | CO$_2$Et | Cl | H | H | H | H | 402.84 | 401 |
| 135 | H | CO$_2$Na | Cl | H | H | H | H | 396.76 | 373 |

TABLE 7

| Compound | R1 | R2 | R3 | R4 | R5 | MW | MS (m/z) |
|---|---|---|---|---|---|---|---|
| 136 | H | CF$_3$ | H | H | H | 379.29 | 378 |
| 137 | H | Cl | H | H | H | 345.74 | 344, 346 |

TABLE 8

| Compound | R1 | R2 | R3 | R4 | R5 | MW | MS (m/z) |
|---|---|---|---|---|---|---|---|
| 138 | H | Cl | H | H | H | 345.78 | 344, 346 |
| 139 | H | CF$_3$ | H | H | H | 379.37 | 378 |
| 140 | H | Br | H | H | H | 390.24 | 389, 391 |
| 141 | H | Cl | Cl | H | H | 380.23 | 378, 380, 382 |

TABLE 9

| Compound | R1 | R2 | R3 | R4 | R5 | MW | MS (m/z) |
|---|---|---|---|---|---|---|---|
| 142 | H | CF₃ | H | H | H | 379.34 | 378 |
| 143 | H | Cl | H | H | H | 345.78 | 344, 346 |
| 144 | H | Br | H | H | H | 390.24 | 389, 391 |
| 145 | H | Cl | Cl | H | H | 380.23 | 378, 380, 382 |
| 146 | H | CF₃ | H | CF₃ | H | 447.33 | 446 |
| 147 | H | CN | H | H | H | 336.35 | 335 |
| 148 | H | CF₃ | F | H | H | 397.32 | 396 |

TABLE 10

| Compound | R1 | R2 | R3 | R4 | R5 | MW | MS (m/z) |
|---|---|---|---|---|---|---|---|
| 149 | H | Cl | H | H | H | 370.20 | 368 |
| 150 | H | Br | H | H | H | 325.75 | 324, 326 |
| 151 | H | CF₃ | H | H | H | 359.30 | 358 |
| 152 | H | Cl | Cl | H | H | 360.20 | 358, 360, 362 |

The names of the compounds shown in Tables 1–10 are given in Table 11. These names were generated with the Chemistry 4-D Draw™ software from ChemInnovation Software, Inc. (San Diego, Calif.).

TABLE 11

| Compound | IUPAC Name |
|---|---|
| 1 | 2H,3H-Benzo[e]1,4-dioxan-6-yl-N-{[(3-chlorophenyl)amino]carbonyl}carboxamide |
| 2 | 2H,3H-Benzo[e]1,4-dioxan-6-yl-N-{[(3,4-dichlorophenyl)amino]carbonyl}carboxamide |
| 3 | 2H,3H-Benzo[e]1,4-dioxan-6-yl-N-{[(3-chloro-4-hydroxyphenyl)amino]carbonyl}carboxamide |
| 4 | 2H,3H-Benzo[e]1,4-dioxan-6-yl-N-({[4-(trifluoromethyl)phenyl]amino}carbonyl)carboxamide |
| 5 | 2H,3H-Benzo[e]1,4-dioxan-6-yl-N-{[(4-chlorophenyl)amino]carbonyl}carboxamide |
| 6 | 2H,3H-Benzo[e]1,4-dioxan-6-yl-N-{[(3-bromophenyl)amino]carbonyl}carboxamide |
| 7 | 2H,3H-Benzo[e]1,4-dioxan-6-yl-N-{[(3-cyanophenyl)amino]carbonyl}carboxamide |
| 8 | 2H,3H-Benzo[e]1,4-dioxan-6-yl-N-{[(2,4-dichlorophenyl)amino]carbonyl}carboxamide |
| 9 | 2H,3H-Benzo[e]1,4-dioxan-6-yl-N-{[(4-iodophenyl)amino]carbonyl}carboxamide |
| 10 | 2H,3H-Benzo[e]1,4-dioxan-6-yl-N-{[(3-iodophenyl)amino]carbonyl}carboxamide |
| 11 | 2H,3H-Benzo[e]1,4-dioxan-6-yl-N-({[3-(trifluoromethoxy)phenyl]amino}carbonyl)carboxamide |
| 12 | 2H,3H-Benzo[e]1,4-dioxan-6-yl-N-({[3-(methylethyl)phenyl]amino}carbonyl)carboxamide |
| 13 | 2H,3H-Benzo[e]1,4-dioxan-6-yl-N-{[(3-methylphenyl)amino]carbonyl}carboxamide |
| 14 | 2H,3H-Benzo[e]1,4-dioxan-6-yl-N-{[(2-iodophenyl)amino]carbonyl}carboxamide |
| 15 | 2H,3H-Benzo[3,4-e]1,4-dioxin-6-yl-N-({[3-(trifluoromethyl)phenyl]amino}carbonyl)carboxamide |
| 16 | 2H,3H-Benzo[3,4-e]1,4-dioxin-6-yl-N-({[3-(trifluoromethylthio)phenyl]amino}carbonyl)carboxamide |
| 17 | 2H,3H-Benzo[3,4-e]1,4-dioxin-6-yl-N-{[(3-ethylphenyl)amino]carbonyl}carboxamide |
| 18 | 2H,3H-Benzo[3,4-e]1,4-dioxin-6-yl-N-{[(3-ethoxyphenyl)amino]carbonyl}carboxamide |
| 19 | 2H,3H-Benzo[3,4-e]1,4-dioxin-6-yl-N-({[3-(methylethoxy)phenyl]amino}carbonyl)carboxamide |
| 20 | 2H,3H-Benzo[3,4-e]1,4-dioxin-6-yl-N-{[(3-phenylphenyl)amino]carbonyl}carboxamide |
| 21 | 2H,3H-Benzo[3,4-e]1,4-dioxin-6-yl-N-({[3-(tert-butyl)phenyl]amino}carbonyl)carboxamide |
| 22 | 2H,3H-Benzo[3,4-e]1,4-dioxin-6-yl-N-{[(3-chloro-4-methylphenyl)amino]carbonyl}carboxamide |
| 23 | 2H,3H-Benzo[3,4-e]1,4-dioxin-6-yl-N-{[(3-iodo-4-methylphenyl)amino]carbonyl}carboxamide |
| 24 | 2H,3H-Benzo[3,4-e]1,4-dioxin-6-yl-N-({[4-methyl-3-(trifluoromethyl)phenyl]amino}carbonyl)-carboxamide |
| 25 | 2H,3H-Benzo[3,4-e]1,4-dioxin-6-yl-N-({[4-fluoro-3-(trifluoromethyl)phenyl]amino}carbonyl)-carboxamide |
| 26 | 2H,3H-Benzo[3,4-e]1,4-dioxin-6-yl-N-({[3,4-bis(trifluoromethyl)phenyl]amino}carbonyl)carboxamide |
| 27 | 2H,3H-Benzo[3,4-e]1,4-dioxin-6-yl-N-({[3,5-bis(trifluoromethyl)phenyl]amino}carbonyl)carboxamide |
| 28 | 2H,3H-Benzo[e]1,4-dioxan-6-yl-N-({[4-chloro-3-(trifluoromethyl)phenyl]amino}carbonyl)carboxamide |
| 29 | 2H,3H-Benzo[e]1,4-dioxan-6-yl-N-{[(3-phenoxyphenyl)amino]carbonyl}carboxamide |
| 30 | 2H,3H-Benzo[e]1,4-dioxan-6-yl-N-{[(3-nitrophenyl)amino]carbonyl}carboxamide |
| 31 | 2H,3H-Benzo[e]1,4-dioxan-6-yl-N-{[(3,5-dichlorophenyl)amino]carbonyl}carboxamide |
| 32 | 2H,3H-Benzo[e]1,4-dioxan-6-yl-N-{[(3-acetylphenyl)amino]carbonyl}carboxamide |
| 33 | Methyl 3-{[(2H,3H-benzo[e]1,4-dioxan-6-ylcarbonylamino)carbonyl]amino}benzoate |
| 34 | 2H,3H-Benzo[e]1,4-dioxan-6-yl-N-{[(3-(1H-1,2,3,4-tetrazol-5-yl)phenyl)amino]carbonyl}carboxamide |
| 35 | 2H,3H-Benzo[3,4-e]1,4-dioxin-6-yl-N-{[(3-ethynylphenyl)amino]carbonyl}carboxamide |
| 36 | 2H,3H-Benzo[3,4-e]1,4-dioxin-6-yl-N-{[(3-chloro-2-methylphenyl)amino]carbonyl}carboxamide |
| 37 | 2H,3H-Benzo[3,4-e]1,4-dioxin-6-yl-N-{[(5-chloro-2-methylphenyl)amino]carbonyl}carboxamide |
| 38 | 2H,3H-Benzo[3,4-e]1,4-dioxin-6-yl-N-{[(5-iodo-2-methylphenyl)amino]carbonyl}carboxamide |
| 39 | 2H,3H-Benzo[3,4-e]1,4-dioxin-6-yl-N-{[(5-chloro-2-methoxyphenyl)amino]carbonyl}carboxamide |

TABLE 11-continued

| Compound | IUPAC Name |
|---|---|
| 40 | 2H,3H-Benzo[3,4-e]1,4-dioxin-6-yl-N-{[(3-chloro-2,6-diethylphenyl)amino]carbonyl}carboxamide |
| 41 | 2H,3H-Benzo[3,4-e]1,4-dioxin-6-yl-N-{[(3-(1,3-thiazol-2-yl)phenyl)amino]carbonyl}carboxamide |
| 42 | 2H,3H-Benzo[e]1,4-dioxan-6-yl-N-{[(3-(2-thienyl)phenyl)amino]carbonyl}carboxamide |
| 43 | 2H,3H-Benzo[e]1,4-dioxan-6-yl-N-{[(3-(3-thienyl)phenyl)amino]carbonyl}carboxamide |
| 44 | 2H,3H-Benzo[e]1,4-dioxan-6-yl-N-{[(3-(2-furyl)phenyl)amino]carbonyl}carboxamide |
| 45 | 2H,3H-Benzo[e]1,4-dioxan-6-yl-N-{[(3-(2-pyridyl)phenyl)amino]carbonyl}carboxamide |
| 46 | 2H,3H-Benzo[e]1,4-dioxan-6-yl-N-{[(4-(1H-1,2,3,4-tetrazol-5-yl)phenyl)amino]carbonyl}carboxamide |
| 47 | Methyl 5-{1[(2H,3H-benzo[e]1,4-dioxan-6-ylcarbonylamino)carbonyl]amino}-2-bromobenzoate |
| 48 | 3-{[(2H,3H-Benzo[e]1,4-dioxan-6-ylcarbonylamino)carbonyl]amino}-5-(trifluoromethyl)benzoic acid |
| 49 | 2H,3H-Benzo[e]1,4-dioxan-6-yl-N-({[3-hydroxy-5-(trifluoromethyl)phenyl]amino}carbonyl)carboxamide |
| 50 | 5-{[(2H,3H-Benzo[e]1,4-dioxan-6-ylcarbonylamino)carbonyl]amino}-2-bromobenzoic acid |
| 51 | 4-{[(2H,3H-Benzo[e]1,4-dioxan-6-ylcarbonylamino)carbonyl]amino}-2-chlorophenyl acetate |
| 52 | 4-{[(2H,3H-Benzo[e]1,4-dioxan-6-ylcarbonylamino)carbonyl]amino}-2-chlorophenyl methyl propane-1,3-dioate |
| 53 | 2-[(4-{[(2H,3H-Benzo[e]1,4-dioxan-6-ylcarbonylamino)carbonyl]amino}-2-chlorophenyl)-oxycarbonyl]acetic acid |
| 54 | Methyl 2-(4-{[(2H,3H-Benzo[e]1,4-dioxan-6-ylcarbonylamino)carbonyl]amino}-2-chlorophenoxy)acetate |
| 55 | 2-(4-{[(2H,3H-Benzo[e]1,4-dioxan-6-ylcarbonylamino)carbonyl]amino}-2-chlorophenoxy)acetic acid |
| 56 | Phenylmethyl 2-(4-{[(2H,3H-benzo[e]1,4-dioxan-6-ylcarbonylamino)carbonyl]amino}-2-chlorophenoxy)acetate |
| 57 | Sodium 4-{[(2H,3H-benzo[e]1,4-dioxan-6-ylcarbonylamino)carbonyl]amino}-2-chlorobenzoate |
| 58 | 5-{[(2H,3H-Benzo[3,4-e]1,4-dioxin-6-ylcarbonylamino)carbonyl]amino}-2-chlorobenzoic acid |
| 59 | Sodium 4-{[(2H,3H-benzo[3,4-e]1,4-dioxin-6-ylcarbonylamino)carbonyl]amino}benzoate |
| 60 | Sodium 3-{[(2H,3H-Benzo[3,4-e]1,4-dioxin-6-ylcarbonylamino)carbonyl]amino}benzoate |
| 61 | 2H,3H-benzo[3,4-e]1,4-dioxin-6-yl-N-{[(2-chloro(4-pyridyl))amino]carbonyl}carboxamide |
| 62 | 2H,3H-benzo[3,4-e]1,4-dioxin-6-yl-N-{[(6-chloro-4-methylpyrimidin-2-yl)amino]carbonyl}carboxamide |
| 63 | 2H,3H-benzo[3,4-e]1,4-dioxin-6-yl-N-({[5-(trifluoromethyl)(1,3,4-thiadiazol-2-yl)]amino}carbonyl)-carboxamide |
| 64 | 2H,3H-Benzo[3,4-e]1,4-dioxin-6-yl-N-{[(3-chlorophenyl)(methoxymethyl)amino]carbonyl}-N-(methoxymethyl)carboxamide |
| 65 | 2H,3H-Benzo[3,4-e]1,4-dioxin-6-yl-N-{[(3-chlorophenyl)amino]carbonyl}-N-[(2-methoxyethoxy)-methyl]carboxamide |
| 66 | N-{[(3-Chlorophenyl)amino]carbonyl}quinoxalin-6-ylcarboxamide |
| 67 | N-{[(3-Bromophenyl)amino]carbonyl}quinoxalin-6-ylcarboxamide |
| 68 | Quinoxalin-6-yl-N-({[4-(trifluoromethyl)phenyl]amino}carbonyl)carboxamide |
| 69 | Quinoxalin-6-yl-N-({[3-(trifluoromethyl)phenyl]amino}carbonyl)carboxamide |
| 70 | Quinoxalin-6-yl-N-({[3-(trifluoromethoxy)phenyl]amino}carbonyl)carboxamide |
| 71 | N-({[3-(Methylethyl)phenyl]amino}carbonyl)quinoxalin-6-ylcarboxamide |
| 72 | N-({[3-(Methylethoxy)phenyl]amino}carbonyl)quinoxalin-6-ylcarboxamide |
| 73 | N-({[4-Fluoro-3-(trifluoromethyl)phenyl]amino}carbonyl)quinoxalin-6-ylcarboxamide |
| 74 | N-{[(3-Chloro-4-hydroxyphenyl)amino]carbonyl}quinoxalin-6-ylcarboxamide |
| 75 | N-({[4-Chloro-3-(trifluoromethyl)phenyl]amino}carbonyl)quinoxalin-6-ylcarboxamide |
| 76 | N-{[(3-Cyanophenyl)amino]carbonyl}quinoxalin-6-ylcarboxamide |
| 77 | N-{[(2,4-Dichlorophenyl)amino]carbonyl}quinoxalin-6-ylcarboxamide |
| 78 | N-{[(3-Phenylphenyl)amino]carbonyl}quinoxalin-6-ylcarboxamide |
| 79 | N-({[3-(Methylethoxy)phenyl]amino}carbonyl)quinoxalin-6-ylcarboxamide |
| 80 | N-{[(3-Phenoxyphenyl)amino]carbonyl}quinoxalin-6-ylcarboxamide |
| 81 | N-({[3,5-bis(Trifluoromethyl)phenyl]amino}carbonyl)quinoxalin-6-ylcarboxamide |
| 82 | N-{[(3,4-Dichlorophenyl)amino]carbonyl}quinoxalin-6-ylcarboxamide |
| 83 | Methyl 2-chloro-5-{[(quinoxalin-6-ylcarbonylamino)carbonyl]amino}benzoate |
| 84 | Ethyl 2-chloro-5-{[(quinoxalin-6-ylcarbonylamino)carbonyl]amino}benzoate |
| 85 | Sodium 2-chloro-5-{[(quinoxalin-6-ylcarbonylamino)carbonyl]amino}benzoate |
| 86 | Sodium 4-{[(quinoxalin-6-ylcarbonylamino)carbonyl]amino}benzoate |
| 87 | Ethyl 2-(2-chloro-4-{[(quinoxalin-6-ylcarbonylamino)carbonyl]amino}phenoxy)acetate |
| 88 | Sodium 2-(2-chloro-4-{[(quinoxalin-6-ylcarbonylamino)carbonyl]amino}phenoxy)acetate |
| 89 | Sodium 3-{[(quinoxalin-6-ylcarbonylamino)carbonyl]amino}benzoate |
| 90 | Sodium 6-chloro-2-{[(quinoxalin-6-ylcarbonylamino)carbonyl]amino}benzoate |
| 91 | Sodium 2-(methylethoxy)-4-{[(quinoxalin-6-ylcarbonylamino)carbonyl]amino}benzoate |
| 92 | Sodium 3-{[(quinoxalin-6-ylcarbonylamino)carbonyl]amino}-5-(trifluoromethyl)benzoate |
| 93 | 2-Chloro-4-{[(quinoxalin-6-ylcarbonylamino)carbonyl]amino}benzoic acid |
| 94 | 2-Hydroxy-4-{[(quinoxalin-6-ylcarbonylamino)carbonyl]amino}benzoic acid |
| 95 | Quinoxalin-6-yl-N-{[(3-(3-thienyl)phenyl)amino]carbonyl}carboxamide |
| 96 | Quinoxalin-6-yl-N-{[(3-(1,3-thiazol-2-yl)phenyl)amino]carbonyl}carboxamide |
| 97 | N-{[(3-(2-Furyl)phenyl)amino]carbonyl}quinoxalin-6-ylcarboxamide |
| 98 | 2-Chloro-4-{[(quinoxalin-6-ylcarbonylamino)carbonyl]amino}benzoicacid |
| 99 | N-{[(3-(2-Pyridyl)phenyl)amino]carbonyl}quinoxalin-6-ylcarboxamide |
| 100 | Quinoxalin-6-yl-N-{[(3-(2-thienyl)phenyl)amino]carbonyl}carboxamide |
| 101 | 2-Phenoxy-4-{[(quinoxalin-6-ylcarbonylamino)carbonyl]amino}benzoic acid |
| 102 | N-({[3-(Phenylcarbonyl)phenyl]amino}carbonyl)quirioxalm-6-ylcarboxamide |
| 103 | Methylethyl 2-chloro-5-{[(quinoxalin-6-ylcarbonylamino)carbonyl]amino}benzoate |
| 104 | 5-Chloro-2-{[(quinoxalin-6-ylcarbonylamino)carbonyl]amino}benzoic acid |
| 105 | Methyl 4-{[(quinoxalin-6-ylcarbonylamino)carbonyl]amino}-2-(trifluoromethyl)benzoate |
| 106 | Methyl 2-hydroxy-4-{[(quinoxalin-6-ylcarbonylamino)carbonyl]amino}benzoate |
| 107 | Phenylmethyl 2-(2-chloro-4-{[(quinoxalin-6-ylcarbonylamino)carbonyl]amino}phenoxy)acetate |
| 108 | 2-(2-Chloro-4-{[(quinoxalin-6-ylcarbonylamino)carbonyl]amino}phenoxy)acetic acid |
| 109 | 2,3-Dimethylquinoxalin-6-yl)-N-{[(3-chlorophenyl)amino]carbonyl}carboxamide |
| 110 | (2,3-Dimethylquinoxalin-6-yl)-N-{[(3-bromophenyl)amino]carbonyl}carboxamide |

TABLE 11-continued

| Compound | IUPAC Name |
|---|---|
| 111 | (2,3-Dimethylquinoxalin-6-yl)-N-({[3-(trifluoromethyl)phenyl]amino}carbonyl)carboxamide |
| 112 | N-{[(3,4-Dichlorophenyl)amino]carbonyl}(2,3-dimethylquinoxalin-6-yl)carboxamide |
| 113 | (2,3-Dimethylquinoxalin-6-yl)-N-{[(3-cyanophenyl)amino]carbonyl}carboxamide |
| 114 | 1,2,3,4-Tetrahydroquinoxalin-6-yl-N-({[4-(trifluoromethyl)phenyl]amino}carbonyl)carboxamide |
| 115 | N-{[(3-Chlorophenyl)amino]carbonyl}-1,2,3,4-tetrahydroquinoxalin-6-ylcarboxamide |
| 116 | N-{[(3-Bromophenyl)amino]carbonyl}-1,2,3,4-tetrahydroquinoxalin-6-ylcarboxamide |
| 117 | 1,2,3,4-Tetrahydroquinoxalin-6-yl-N-({[3-(trifluoromethyl)phenyl]amino}carbonyl)carboxamide |
| 118 | (1,4-Diethyl(1,2,3,4-tetrahydroquinoxalin-6-yl))-N-({[3-(trifluoromethyl)phenyl]amino}carbonyl)-carboxamide |
| 119 | 1,2,3,4-Tetrahydroquinoxalin-6-yl-N-({[3-(trifluoromethoxy)phenyl]amino}carbonyl)carboxamide |
| 120 | N-({[3-(Methylethyl)phenyl]amino}carbonyl)-1,2,3,4-tetrahydroquinoxalin-6-ylcarboxamide |
| 121 | N-{[(3-Iodophenyl)amino]carbonyl}-1,2,3,4-tetrahydroquinoxalin-6-ylcarboxamide |
| 122 | N-({[4-Fluoro-3-(trifluoromethyl)phenyl]amino}carbonyl)-1,2,3,4-tetrahydroquinoxalin-6-ylcarboxamide |
| 123 | (1,4-Dimethyl(1,2,3,4-tetrahydroqumoxalin-6-yl))-N-({[3-(trifluoromethyl)phenyl]amino}carbonyl)-carboxamide |
| 124 | N-({[4-Chloro-3-(trifluoromethyl)phenyl]amino}carbonyl)-1,2,3,4-tetrahydroquinoxalin-6-ylcarboxamide |
| 125 | N-{[(3-Cyanophenyl)amino]carbonyl}-1,2,3,4-tetrahydroquinoxalin-6-ylcarboxamide |
| 126 | N-{[(3-Phenylphenyl)amino]carbonyl}-1,2,3,4-tetrahydroquinoxalin-6-ylcarboxamide |
| 127 | N-({(3-(Methylethoxy)phenyl]amino}carbonyl)-1,2,3,4-tetrahydroquinoxalin-6-ylcarboxamide |
| 128 | N-{[(3-Phenoxyphenyl)amino]carbonyl}-1,2,3,4-tetrahydroquinoxalin-6-ylcarboxamide |
| 129 | N-({[3,5-bis(Trifluoromethyl)phenyl]amino}carbonyl)-1,2,3,4-tetrahydroquinoxalin-6-ylcarboxamide |
| 130 | N-{[(3-Chloro-4-hydroxyphenyl)amino]carbonyl}-1,2,3,4-tetrahydroqumoxalin-6-ylcarboxamide |
| 131 | [1,4-bis(2-Hydroxyethyl)(1,2,3,4-tetrahydroquinoxalin-6-yl)]-N-({[3-(trifluoromethyl)phenyl]amino}-carbonyl)carboxamide |
| 132 | [4-(2-Hydroxyethyl)(1,2,3,4-tetrahydroquinoxalin-6-yl)]-N-({[3-(trifluoromethyl)phenyl]amino}-carbonyl)carboxamide |
| 133 | Ethyl 2-(2-chloro-4-{[(1,2,3,4-tetrahydroquinoxalin-6-ylcarbonylamino)carbonyl]amino}phenoxy)acetate |
| 134 | Ethyl 2-chloro-5-{[(1,2,3,4-tetrahydroquinoxalin-6-ylcarbonylamino)carbonyl]amino}benzoate |
| 135 | Sodium 2-chloro-5-{[(1,2,3,4-tetrahydroquinoxalin-6-ylcarbonylamino)carbonyl]amino}benzoate |
| 136 | (3-Oxo(2H,4H-Benzo[3,4-e]1,4-oxazaperhydroin-6-yl))-N-({[3-(trifluoromethyl)phenyl]amino}-carbonyl)carboxamide |
| 137 | N-{[(3-Chlorophenyl)amino]carbonyl}(3-oxo(2H,4H-benzo[3,4-e]1,4-oxazaperhydroin-6-yl))carboxamide |
| 138 | N-{[(3-Chlorophenyl)amino]carbonyl}(4-methyl(2H,3H-benzo[3,4-e]1,4-oxazaperhydroin-6-yl))-carboxamide |
| 139 | (4-Methyl(2H,3H-benzo[3,4-e]1,4-oxazaperhydroin-6-yl))-N-({[3-(trifluoromethyl)phenyl]amino}-carbonyl)carboxamide |
| 140 | N-{[(3-Bromophenyl)amino]carbonyl}(4-methyl(2H,3H-benzo[3,4-e]1,4-oxazaperhydroin-6-yl))-carboxamide |
| 141 | N-{[(3,4-Dichlorophenyl)amino]carbonyl}(4-methyl(2H,3H-benzo[3,4-e]1,4-oxazaperhydroin-6-yl))-carboxamide |
| 142 | (4-Methyl(2H,3H-benzo[e]1,4-oxazin-7-yl))-N-({[3-(trifluoromethyl)phenyl]amino}carbonyl)carboxamide |
| 143 | N-{[(3-Chlorophenyl)amino]carbonyl}(4-methyl(2H,3H-benzo[e]1,4-oxazin-7-yl))carboxamide |
| 144 | N-{[(3-Bromophenyl)amino]carbonyl}(4-methyl(2H,3H-benzo[e]1,4-oxazin-7-yl))carboxamide |
| 145 | N-{[(3,4-Dichlorophenyl)amino]carbonyl}(4-methyl(2H,3H-benzo[e]1,4-oxazin-7-yl))carboxamide |
| 146 | N-({[3,5-bis(Trifluoromethyl)phenyl]amino}carbonyl)(4-methyl(2H,3H-benzo[e]1,4-oxazin-7-yl))-carboxamide |
| 147 | N-{[(3-Cyanophenyl)amino]carbonyl}(4-methyl(2H,3H-benzo[e]1,4-oxazin-7-yl))carboxamide |
| 148 | N-({[4-Fluoro-3-(trifluoromethyl)phenyl]amino}carbonyl)(4-methyl(2H,3H-benzo[e]-1,4-oxazin-7-yl))carboxamide |
| 149 | N-{[(3-Chlorophenyl)amino]carbonyl}-6-quinolylcarboxamide |
| 150 | N-{[(3-Bromophenyl)arnino]carbonyl}-6-quinolylcarboxamide |
| 151 | 6-Quinolyl-N-({[3-(trifluoromethyl)phenyl]amino}carbonyl)carboxamide |
| 152 | N-{[(3,4-Dichlorophenyl)amino]carbonyl}-6-quinolylcarboxamide |

Example 6

Inhibition of MCP-1 Induced Chemotaxis

A 96 well microchemotaxis chamber with a 5 μm-pore size, PVP-coated polycarbonate filter membrane (Neuro Probe Inc., Cabin John, Md.) was used for testing. Compounds were prepared as 10 mM stock solution in DMSO. THP-1 cells (2×10$^6$ cells/mL) were labeled with 5 μM Calcein AM containing 0.1% F127 (Molecular Probe, Eugene, Oreg.) at 37° C. for 30 min, and then pretreated with compound at room temperature for an additional 30 min. The lower chamber was loaded with medium containing 12.5 nM hMCP-1. The filter membrane was placed over the lower chamber, followed by a silicon gasket and the upper chamber. The pretreated THP-1 cells (4×10$^5$ cells/50 μL of RPMI1640 medium per well) were added to the upper chamber and incubated in 5% $CO_2$ at 37° C. for 2 hr. The migrated cells were determined with a fluorescent plate reader (LJL BioSystems, Sunnyvale, Calif.). Table 12 shows the $IC_{50}$ (concentration of compound that inhibited migration of 50% of the cells relative to control) for several compounds of the present invention.

TABLE 12

Effect of Compounds on MCP-1 Induced Chemotaxis

| Compound | $IC_{50}$ (μM) | Compound | $IC_{50}$ (μM) | Compound | $IC_{50}$ (μM) |
|---|---|---|---|---|---|
| 1 | 0.577 | 3 | 4.339 | 5 | >50 |
| 6 | 0.875 | 7 | 0.891 | 8 | 47.885 |
| 9 | >50 | 10 | 0.204 | 11 | 10.476 |
| 12 | 0.789 | 15 | 3.433 | 18 | 2.836 |
| 19 | 0.355 | 20 | 1.46 | 24 | 0.068 |
| 25 | 0.026 | 26 | 4.213 | 27 | 0.406 |
| 29 | 0.024 | 30 | 2.022 | 31 | 1.555 |

TABLE 12-continued

Effect of Compounds on MCP-1 Induced Chemotaxis

| Compound | IC$_{50}$ ($\mu$M) | Compound | IC$_{50}$ ($\mu$M) | Compound | IC$_{50}$ ($\mu$M) |
|---|---|---|---|---|---|
| 32 | 0.788 | 35 | 0.380 | 36 | 0.133 |
| 37 | 8.741 | 38 | 8.743 | 39 | 8.797 |
| 41 | 0.065 | 42 | 0.238 | 43 | 0.173 |
| 44 | 1.367 | 45 | 0.364 | 61 | 3.103 |
| 66 | 3.585 | 67 | 7.479 | 68 | 2.72 |
| 69 | 0.775 | 70 | 1.764 | 71 | 0.493 |
| 72 | 3.429 | 73 | 0.629 | 74 | 1.491 |
| 75 | 0.498 | 76 | 0.629 | 77 | 0.810 |
| 78 | 0.062 | 79 | 0.175 | 80 | 0.094 |
| 81 | 0.324 | 83 | 0.687 | 84 | 0.035 |
| 85 | >50 | 86 | 36.829 | 88 | >50 |
| 89 | 0.741 | 90 | >50 | 91 | 0.266 |
| 92 | >50 | 113 | 6.954 | 115 | 0.995 |
| 117 | 1.981 | 121 | 0.478 | 123 | 15.246 |
| 131 | >50 | 135 | >50 | 141 | 22.003 |
| 143 | 1.326 | 144 | 6.383 | 146 | 9.971 |
| 148 | 16.887 | 151 | 40.471 | | |

Example 7

Thioglycollate-Induced Inflammation Model

3% Brewer's thioglycollate broth (Difco, Detroit, Mich.) was injected into the peritoneal cavity of ICR male mice, followed by subcutaneous administration of the test compounds at the same dose after 0 h, 3 h and 16 hours. After 96 h, the number of total elicited cells and MOMA2-positive cells in the peritoneal cavity was analyzed using an EPICS XL Beckman Coulter. The results are shown in Table 13.

TABLE 13

[a]Effect of Compounds on a Thioglycollate-Induced Inflammation Model

| Compound | Dose (mg/kg) | Total Cells (×10$^6$) | MOMA2-positive Cells (×10$^6$) |
|---|---|---|---|
| No treatment | — | 2.1 ± 0.3** | 1.2 ± 0.2** |
| Control | — | 24.4 ± 1.1 | 18.5 ± 0.9 |
| 55 | 10 | 14.1 ± 1.6** | 10.1 ± 1.5** |
| 59 | 10 | 17.3 ± 1.7** | 13.2 ± 1.4** |
| Anti-MCP-1 Ab | 1 | 12.3 ± 1.8** | 8.8 ± 1.2** |

[a]Anti-MCP-1 Ab was intraperitoneally injected. Significant difference from control group: *P < 0.05, **P < 0.01 (ANOVA).

Example 8

Apolipoprotein E-Deficient Mouse Model

Apolipoprotein E (apoE) is a component of several plasma lipoproteins, including chylomicrons, VLDL, and HDL. Receptor-mediated catabolism of these lipoprotein particles is mediated through the interaction of apoE with the LDL receptor (LDLR) or with LDLR-related protein (LRP). ApoE-deficient mice exhibit hypercholesterolemia and develop complex atheromatous lesions similar to those seen in humans. The efficacy of the compounds of the present invention was also evaluated using this animal model.

Male, 4 week-old apoE-deficient mice were fed on high-fat diet (15% fat, 1.25% cholesterol). The test compound was administered as food admixture for 8 weeks. At 12 weeks old, the mice were fasted for 4 hours and then sacrificed under ether anesthesia. Blood was collected in the presence of heparin, and the hearts were perfused in situ with PBS (pH 7.4), followed by 4% paraformaldehyde for 5 min.

To determine cross-sectional lesion areas, the hearts were embedded in OCT compound and sectioned at 10 $\mu$m using cryostat. The sections were stained with oil red O. Each section of the aortic valve was evaluated for oil red O staining by capturing images directly from a RGB camera attached to a light microscope; image analysis was performed with the IPAP-WIN software (Sumika Tekno, Japan). Five sections were examined for each animal, and the sum of the lesion areas was calculated and expressed as the percent of the total cross-sectional wall area. Total cholesterol was determined with a Determiner assay kit (Kyowa Medex, Japan).

The effect of a representative test compound in this animal model of atherosclerosis is shown in Table 14.

TABLE 14

[a]Effect of Compounds on the ApoE-Deficient Mouse Model of Atherosclerosis

| Compound | Dose (mg/kg) | % Atherosclerotic Lesion (mean ± SD) |
|---|---|---|
| Control | — | 25.08 ± 6.93 |
| 59 | 50 | 21.08 ± 6.86 |
| 55 | 50 | 17.80 ± 3.43* |

[a]Significant difference from control group: *P < 0.05 (t-test).

Example 9

Caerulein-Induced Pancreatitis

Caerulein was injected intraperitoneally to male ICR mice every 1 h for 6 h. The test compound was given orally immediately after the caerulein injection, and then again at 3 h and 6 h. After 15 h, the mice were sacrificed and their blood was collected and analyzed for serum amylase activity as a marker of pancreatitis.

The effect of a representative test compound is shown in Table 15.

TABLE 15

[a]Effect of Compounds on Caerulein-Induced Pancreatitis

| Compound | Dose (mg/kg) | Serum Amylase Level (U, Caraway, mean ± SD) |
|---|---|---|
| No Treatment | — | 1079 ± 98 |
| Control | — | 1531 ± 279 |
| 57 | 20 | 551 ± 157** |
| Anti-MCP-1 | 1 | 1104 ± 222 |

[a]Significant difference from control group: **P < 0.05 (LSD).

Example 10

Oral Pharmaceutical Composition—Solid Dosage Formulation

A pharmaceutical composition for oral administration may be prepared by combining the following:

|  | % w/w |
| --- | --- |
| Compound of this invention | 10.0 |
| Magnesium stearate | 0.5 |
| Starch | 2.0 |
| (hydroxypropyl)methylcellulose | 1.0 |
| Microcrystalline cellulose | 86.5 |

The mixture may be compressed to tablets, or filled into hard gelatin capsules. The tablet may be coated by applying a suspension of film former (e.g., (hydroxypropyl)methylcellulose), pigment (e.g., titanium dioxide) and plasticiser (e.g., diethyl phthalate) and drying the film by evaporation of the solvent. The film coat can comprise 2.0% to 6.0% of the tablet weight, preferably about 3.0%.

Example 11

Oral Pharmaceutical Composition Preparation—Softgel

A pharmaceutical composition of a compound of the invention suitable for oral administration may also be prepared by combining the following:

|  | % w/w |
| --- | --- |
| Compound of this invention | 20 |
| Polyethylene glycol 400 | 80 |

The medicinal compound is dispersed or dissolved in the liquid carrier, with a thickening agent added, if required. The formulation is then enclosed in a soft gelatin capsule by suitable technology.

Example 12

Pharmaceutical Composition for Parenteral Administration

A pharmaceutical composition for parenteral administration may be prepared by combining the following:

|  | Preferred Level (%) |
| --- | --- |
| Compound of this invention | 1.0 |
| Saline | 99.0 |

The solution is sterilized and sealed in sterile containers.

Various modifications and variations of the present invention will be apparent to those skilled in the art without departing from the scope and spirit of the invention. Although the invention has been described in connection with specific preferred embodiments, it should be understood that the invention as disclosed should not be unduly limited to such specific embodiments. Various modifications of the described modes for carrying out the invention which are obvious to those skilled in the art are intended to be within the scope of this invention.

We claim:

1. A compound of formula Ib or formula IIb:

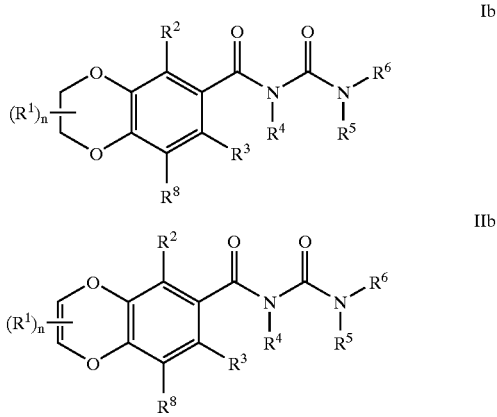

where:
n is an integer of 0 to 4 in Formula Ib, and is an integer of 0 to 2 in Formula IIb;

each $R^1$ is independently optionally substituted lower alkyl, alkenyl, alkynyl, cyloalkyl, cycloalky (lower alkyl), optionally substituted heterocycloalkyl, optionally substituted aryl, optionally substituted heteroaryl, optionally substituted aryl(lower alkyl), halo(lower alkyl), —$CH_3$, halogen, nitro, —CN, —$OR^9$, —$SR^9$, —$NR^9R^{10}$, —$NR^9(CH_2)_{1-6}C(=O)OR^{10}$, —$C(=O)R^9$, $C(=O)OR^9$, —$(=O)NR^9R^{10}$, —$OC(=O)R^9$, —$SO_2R^9$, —$OSO_2R^9$, —$SO_2NR^9R^{10}$, —$NR^9SO_2R^{10}$ or —$NR^9O(=O)R^{10}$, where $R^9$ and $R^{10}$ are independently, hydrogen, optionally substituted lower alkyl, lower alkyl-N($C_{1-2}$ alkyl)$_2$, lower alkyl (optionally substituted heterocycloalkyl), alkenyl, alkynyl, optionally substituted cycloalkyl, cycloalkyl (lower alkyl), optionally substituted heterocycloalkyl (lower alkyl), aryl(lower alkyl), optionally substituted aryl, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N—$(CH_2)_{1-6}C(=O)OR$ (where R is hydrogen or lower alkyl) or N-(optionally substituted $C_{1-2}$ alkyl) group, or in Formula I, n=2 and the two $R^1$'s together constitute =O, $R^2$, $R^3$ and $R^8$ are independently hydrogen, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —$CF_3$, halogen, nitro, —CN, —$OR^9$, —$SR^9$, —$NR^9R^{10}$, —$NR^9(CH_2)_{1-6}C(=O)OR^{10}$, —$C(=O)R^9$, —$(=O)OR^9$, —$C(=O)NR^9R^{10}$, —$OC(=O)R^9$, —$SO_2R^9$, —$OSO_2R^9$, —$SO_2NR^9R^{10}$, —$NR^9SO_2R^{10}$ or —$NR^9C(=O)R^{10}$, where $R^9$ and $R^{10}$ are independently, hydrogen, optionally substituted lower alkyl, lower alky-N($C_{1-2}$ alkyl)$_2$, lower alkyl (optionally substituted heterocycloalkyl), alkenyl, alkynyl, optionally substituted cycloalkyl, cycloalkyl (lower alkyl), optionally substituted heterocycloalkyl (lower alkyl), aryl(lower alkyl), optionally substituted aryl, heteroaryl, heteroaryl(lower alkyl), or $R^9$ and $R^{10}$ together are —$(CH_2)_{4-6}$ optionally interrupted by one O, S, NH, N-(aryl), N-(aryl(lower alkyl), N—(CH$_2$)$_{1-6}$C(=O)OR (where R is hydrogen or lower alkyl) or N-(optionally substituted C$_{1-2}$ alkyl) group, R$^4$ and R$^5$ are independently hydrogen, lower alkyl optionally substituted lower alkyl, optionally substituted aryl, or optionally substituted aryl(lower alkyl), or, together, are —(CH$_2$)$_{2-4}$—, and R$^6$ is hydrogen, optionally substituted lower alkyl, alkenyl, alkynyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O)R$^{11}$, —C(=O)OR$^{11}$, —C(=O)NR$^{11}$R$^{12}$, —SO$_2$R$^{11}$, or —SO$_2$NR$^{11}$R$^{12}$, where R$^{11}$ and R$^{12}$ are independently; hydrogen, optionally substituted lower alkyl, alkenyl, alkynyl, cycloalkyl, cycloalkyl(lower alkyl), optionally substituted aryl, heteroaryl, heteroaryl(lower alkyl), or R$^{11}$ and R$^{12}$ together are —(CH$_2$)$_{4-6}$—, or a pharmaceutically acceptable salt thereof, as a single stereoisomer or mixture of stereoisomers.

2. A compound of claim 1 where Z is CR—R$^8$.

3. A compound of claim 1 where R$^8$ is H.

4. A compound of claim 1 where the compound is a compound of Formula Ib, or a pharmaceutically acceptable salt thereof, as a single stereoisomer or mixture of stereoisomers.

5. A compound of claim 1 where the compound is a compound of Formula IIb, or a pharmaceutically acceptable salt thereof, as a single stereoisomer or mixture of stereoisomers.

6. A compound of claim 1 where each R$^1$ is independently, optionally substituted lower alkyl, optionally substituted heterocycloalkyl, optionally substituted aryl, optionally substituted heteroaryl, optionally substituted aryl(lower alkyl) halogen, —OR$^9$, —NR$^9$R$^{10}$, —C(=O)OR$^9$, —C(=O)NR$^9$R$^{10}$, —SO$_2$NR$^9$R$^{10}$, or —NR$^9$C(=O)R$^{10}$, where R$^9$ and R$^{10}$ are independently, hydrogen, optionally substituted lower alkyl, lower alkyl-N(C$_{1-2}$ alkyl)$_2$, lower alkyl (optionally substituted heterocycloalkyl), aryl(lower alkyl), optionally substituted aryl, heteroaryl, or heteroaryl(lower alkyl).

7. A compound of claim 1 where n=0.

8. A compound of claim 1 where R$^2$ is optionally substituted lower alkyl, cycloalkyl, optionally substituted heterocycloalkyl, optionally substituted aryl, optionally substituted heteroaryl, optionally substituted aryl(lower alkyl), halogen, —OR$^9$, —NR$^9$(CH$_2$)$_{1-6}$C(=O)OR$^{10}$, —C(=O)OR$^9$, —C(=O)NR$^9$R$^{10}$, —SO$_2$NR$^9$R$^{10}$, or —NR$^9$C(=O)R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, heteroaryl, heteroaryl(lower alkyl), or R$^9$ and R$^{10}$ together are —(CH$_4$)$_{4-6}$— optionally interrupted by one O, S, NH, N-(aryl), N-(aryl(lower alkyl), N—(CH$_2$)$_{1-6}$C(=O)OR (where R is hydrogen or lower alkyl) or N-(optionally substituted C$_{1-2}$ alkyl) group.

9. A compound of claim 1 where R$^2$ is —NR$^9$R$^{10}$, wherein R$^9$ and R$^{10}$ are independently, hydrogen, optionally substituted lower alkyl, lower alkyl-N(C$_{1-2}$ alkyl)$_2$, lower alkyl (optionally substituted heterocycloalkyl), alkenyl, alkynyl, optionally substituted cycloalkyl, cycloalkyl(lower alkyl), benzyl, optionally substituted aryl, heteroaryl, heteroaryl (lower alkyl), or R$^9$ and R$^{10}$ together are —(CH$_2$)$_{4-6}$— optionally interrupted by one O, S, NH, N-(aryl), N-(aryl (lower alkyl)), N-(CH$_2$)$_{1-6}$C(=O)OR (where R is hydrogen or lower alkyl) or N-(optionally substituted C$_{1-2}$ alkyl) group.

10. A compound of claim 1 where R$^2$ is hydrogen.

11. A compound of claim 1 where the compound is a compound of formula Ib, where R$^8$ is H, n=0, and R$^2$ is hydrogen, or a pharmaceutically acceptable salt thereof, as a single stereoisomer or mixture of stereoisomers.

12. A compound of claim 1 where R$^3$ is optionally substituted lower alkyl, optionally substituted heterocycloalkyl, optionally substituted aryl, optionally substituted heteroaryl, optionally substituted aryl(lower alkyl), halo(lower alkyl), halogen, —OR$^9$, —NR$^9$R$^{10}$, —C(=O) OR$^9$, or —C(=O)NR$^9$R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, heteroaryl, heteroaryl(lower alkyl), or R$^9$ and R$^{10}$ together are —(CH$^2$)$_{4-6}$— optionally interrupted by one O, S, NH, N-(aryl), N-(aryl(lower alkyl)), N-(CH$_2$)$_{1-6}$C(=O)OR (where R is hydrogen or lower alkyl) or N-(optionally substituted C$_{1-2}$ alkyl group.

13. A compound of claim 1 where R$^3$ is hydrogen.

14. A compound of claim 1 where R$^4$ and R$^5$ are independently hydrogen or lower alkyl.

15. A compound of claim 1 where R$^6$ is hydrogen, optionally substituted lower alkyl, alkenyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O) R$^{11}$, —C(=O)OR$^{11}$, —C(=O)NR$^{11}$R$^{12}$, —SO$_2$R$^{11}$, or —SO$_2$NR$^{11}$R$^{12}$, where R$^{11}$ and R$^{12}$ are independently, hydrogen, optionally substituted lower alkyl, cycloalkyl, cycloalkyl(lower alkyl), aryl, heteroaryl, heteroaryl(lower alkyl), or R$^{11}$ and R$^{12}$ together are —(CH$_2$)$_{4-6}$—.

16. A compound of claim 1 where:

R$^6$ is m is an integer of 0 to 4;

R$^{13}$ is hydrogen, optionally substituted lower alkyl), alkenyl, alkynyl, cycloalkyl, cycloalkyl(lower alkyl), heterocycloalkyl, optionally substituted aryl, optionally substituted aryl(lower alkyl, optionally substituted heteroaryl, optionally substituted heteroaryl(lower alkyl), halo(lower alkyl), —CF$_3$, halogen, nitro, —CN, —OR$^{15}$, —SR$^{15}$, —NR$^{15}$R$^{16}$, —C(=O)R$^{15}$, —C(=O)OR$^{15}$, —C(=O)NR$^{15}$R$^{16}$, —OC(=O)R$^{15}$, —SO$_2$R$^{15}$, —SO$_2$NR$^{15}$R$^{16}$, NR$^{15}$SO$_2$R$^{16}$ or —NR$^{15}$C (=O)R$^{16}$, where R$^{15}$ and R$^{16}$ are independently hydrogen, optionally substituted lower alkyl, alkenyl, alkynyl, —CF$_3$, cycloalkyl, optionally substituted heterocycloalkyl, cycloalkyl(lower alkyl), optionally substituted aryl, optionally substituted heteroaryl, optionally substituted heteroaryl(lower alkyl), or, together, are —(CH$_2$)$_{4-6}$— optionally interrupted by one O, S, NH or N—(C$_{1-2}$ alkyl) group, and each R$^{14}$ is independently optionally substituted lower alkyl, optionally substituted aryl, optionally substituted heteroaryl, hydroxy, halogen, —CF$_3$, —OR$^{17}$, —NR$^{17}$R$^{18}$, —C(=O) R$^{17}$, —C(=O)OR$^{17}$, —C(=O)NR$^{17}$R$^{18}$, where R$^{17}$ and R$^{18}$ are independently, hydrogen, lower alkyl, alkenyl, alkynyl, —CF$_3$, optionally substituted heterocycloalkyl, cycloalkyl, cycloalkyl(lower alkyl), optionally substituted aryl, heteroaryl, heteroaryl(lower alkyl), or, together, are —(CH$_2$)$_{4-6}$—, optionally interrupted by one O, S, NH or N—(C$_{1-2}$ alky) group.

17. A compound of claim 16 where R$^{15}$ is hydrogen, optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —OR$^{15}$, —SR$^{15}$, —NR$^{15}$R$^{16}$, —C(=O)R$^{15}$, —C(=O)OR$^{15}$, —C(=O)NR$^{15}$R$^{16}$, —OC(=O)R$^{15}$, —SO$_2$R$^{15}$, —SO$_2$NR$^{15}$R$^{16}$, or —NR$^{15}$C(=O)R$^{16}$, where R$^{15}$ and R$^{16}$ are independently hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl (lower alkyl) or, together, are —(CH$_2$)$_{4-6}$— optionally interrupted by one O, S, NH or N—(C$_{1-2}$ alkyl) group.

18. A compound of claim 17 where R$^{13}$ is optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —OR$^{15}$, —SR$^{15}$, —NR$^{15}$R$^{16}$, —C(=O)R$^{15}$, —C(=O)OR$^{15}$, —C(=O)NR$^{15}$R$^{16}$, —OC(=O)R$^{15}$, —SO$_2$R$^{15}$, —SO$_2$NR$^{15}$R$^{16}$, or —NR$^{15}$C(=O)R$^{16}$, where R$^{15}$ and R$^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —(CH$_2$)$_{4-6}$— optionally interrupted by one O, S, NH or N—(C$_{1-2}$ alkyl) group.

19. A compound of claim 18 where R$^{13}$ is independently selected from aryl, substituted aryl, optionally substituted heteroaryl, halogen, —CF$_3$, —CN, —OR$^{15}$, or —C(=O)OR$^{15}$, where R$^{15}$ is hydrogen, lower alkyl or optionally substituted aryl.

20. A compound of claim 16 where each R$^{14}$ is independently selected from optionally substituted lower alkyl, optionally substituted aryl, optionally substituted heteroaryl, hydroxy, halogen, —CF$_3$, —OR$^{17}$—NR$^{17}$R$^{18}$, —C(=O)OR$^{18}$, —C(=O)OR$^{18}$, and —C(=O)NR$^{17}$R$^{18}$, where R$^{17}$ and R$^{18}$ are, independently, hydrogen, lower alkyl, alkenyl, or optionally substituted aryl.

21. A compound of claim 16 where each R$^{14}$ is independently selected from halogen, —CF$_3$, —OR$^{17}$, —C(=O)OR$^{17}$, or —OCH$_2$C(=O)OR$^{17}$, where R$^{17}$ is hydrogen, lower alkyl or optionally substituted aryl.

22. A compound of claim 16 where R$^{13}$ is not hydrogen, and m is an integer of 1 to 2.

23. A compound of claim 22 where in m is 1.

24. A compound of claim 16 where R$^2$ and R$^3$ are independently selected from hydrogen, lower alkyl, and halogen.

25. A compound of claim 1 that is selected from the group consisting of:

2H,3H-benzo[e]1,4-dioxan-6-yl-N-{[(3-chlorophenyl)amino]carbonyl}carboxamide;
2H,3H-benzo[e]1,4-dioxan-6-yl-N-{[(3,4-dichlorophenyl)amino]carbonyl}carboxamide;
2H,3H-benzo[e]1,4-dioxan-6-yl-N-{[(3-chloro-4-hydroxyphenyl)amino]carbonyl}carboxamide;
2H,3H-benzo[e]1,4-dioxan-6-yl-(N-{[4-(trifluoromethyl)phenyl]amino}carbonyl)carboxamide;
2H,3H-benzo[e]1,4-dioxan-6-yl-N-{[(4-chlorophenyl)amino]carbonyl}carboxamide;
2H,3H-benzo[e]1,4-dioxan-6-yl-N-{[(3-bromophenyl)amino]carbonyl}carboxamide;
2H,3H-benzo[e]1,4-dioxan-6-yl-N-{[(3-cyanophenyl)amino]carbonyl}carboxamide;
2H,3H-benzo[e]1,4-dioxan-6-yl-N-{[(2,4-dichlorophenyl)amino]carbon}carboxamide;
2H,3H-benzo[e]1,4-dioxan-6-yl-N-{[(4-iodophenyl)amino]carbonyl}carboxamide;
2H,3H-benzo[e]1,4-dioxan-6-yl-N-{[(3-iodophenyl)amino]carbonyl}carboxamide;
2H,3H-benzo[e]1,4-dioxan-6-yl-N-({[3-(trifluoromethoxy)phenyl]amino}carbonyl)carboxamide;
2H,3H-benzo[e]1,4-dioxan-6-yl-N-({[(3-(methylethyl)phenyl]amino}carbonyl)carboxamide;
2H,3H-benzo[e]1,4-dioxan-6-yl-N-{[(3-(methylphenyl)amino]carbonyl}carboxamide;
2H,3H-benzo[e]1,4-dioxan-6-yl-N-{[(2-iodophenyl)amino]carbonyl}carboxamide;
2H,3H-benzo[3,4-e]1,4-dioxin-6-yl-N-({[(3-(trifluoromethyl)phenyl]amino}carbonyl)carboxamide;
2H,3H-benzo[3,4-e]1,4-dioxin-6-yl-N-({[(3-(trifluoromethylthio)phenyl]amino}carbonyl)carboxamide;
2H,3H-benzo[3,4-e]1,4-dioxin-6-yl-N-{[(3-ethylphenyl)amino]carbonyl}carboxamide;
2H,3H-benzo[3,4-e]1,4-dioxin-6-yl-N-{[(3-ethoxyphenyl)amino]carbonyl}carboxamide;
2H,3H-benzo[3,4-e]1,4-dioxin-6-yl-N-({[3-(methylethoxy)phenyl]amino}carbonyl)carboxamide;
2H,3H-benzo[3,4-e]1,4-dioxin-6-yl-N-{[(3-phenylphenyl)amino]carbonyl}carboxamide;
2H,3H-benzo[3,4-e]1,4-dioxin-6-yl-N-({[3-(tert-butyl)phenyl]amino}carbonyl)carboxamide;
2H,3H-benzo[3,4-e]1,4-dioxin-6-yl-N-{[(3-chloro-4-methylphenyl)amino]carbonyl}carboxamide;
2H,3H-benzo[3,4-e]1,4-dioxin-6-yl-N-{[(3-iodo-4-methylphenyl)amino]carbonyl}carboxamide;
2H,3H-benzo[3,4-e]1,4-dioxin-6-yl-N-({[4-methyl-3-(trifluoromethyl)phenyl]amino}carbonyl)-carboxamide;
2H,3H-benzo[3,4-e]1,4-dioxin-6-yl-N-({[4-fluoro-3-(trifluoromethyl)phenyl]amino}carbonyl)-carboxamide;
2H,3H-benzo[3,4-e]1,4-dioxin-6-yl-N-{[(3,4-bis(trifluoromethyl)phenyl]amino}carbonyl)carboxamide;
2H,3H-benzo[3,4-e]1,4-dioxin-6-yl-N-({[3,5-bis(trifluoromethyl)phenyl]amino}carbonyl)carboxamide;
2H,3H-benzo[e]1,4-dioxan-6-yl-N-({[4-chloro-3-(trifluoromethyl)phenyl]amino}carbonyl)carboxamide;
2H,3H-benzo[e]1,4-dioxan-6-yl-N-{[(3-phenoxyphenyl)amino]carbonyl}carboxamide;
2H,3H-benzo[e]1,4-dioxan-6-yl-N-{[(3-nitrophenyl)amino]carbonyl}carboxamide;
2H,3H-benzo[e]1,4-dioxan-6-yl-N-{[(3,5-dichlorophenyl)amino]carbonyl}carboxamide;
2H,3H-benzo[e]1,4-dioxan-6-yl-N-{[(3-acetylphenyl)amino]carbonyl}carboxamide;
methyl 3-{[(2H,3H-benzo[e]1,4-dioxan-6-ylcarbonylamino)carbonyl]amino}benzoate;
2H,3H-benzo[e]1,4-dioxan-6-yl-N-{[(3-(1H-1,2,3,4-tetrazol-5-yl)phenyl)amino]carbonyl}carboxamide;
2H,3H-benzo[3,4-e]1,4-dioxin-6-yl-N-{[(3-ethynylphenyl)amino]carbonyl}carboxamide;
2H,3H-benzo[3,4-e]1,4-dioxin-6-yl-N-{[(3-chloro-2-methylphenyl)amino]carbonyl}carboxamide;
2H,3H-benzo[3,4-e]1,4-dioxin-6-yl-N-{[(5-chloro-2-methylphenyl)amino]carbonyl}carboxamide;
2H,3H-benzo[3,4-e]1,4-dioxin-6-yl-N-{[(5-iodo-2-methylphenyl)amino]carbonyl}carboxamide;
2H,3H-benzo[3,4-e]1,4-dioxin-6-yl-N-{[(5-chloro-2-methoxyphenyl)amino]carbonyl}carboxamide;

2H,3H-benzo[3,4-e]1,4-dioxin-6-yl-N-{[(3-chloro-2,6diethylphenyl)amino]carbonyl}carboxamide;
2H,3H-benzo[3,4-e]1,4-dioxin-6-yl-N-{[(3-(1,3-thiazol-2-yl)phenyl)amino]carbonyl}carboxamide;
2H,3H-benzo[e]1,4-dioxan-6-yl-N-{[(3-(2-thienyl)phenyl)amino]carbonyl}carboxamide;
2H,3H-benzo[e]1,4-dioxan-6-yl-N-{[(3-(3-thienyl)phenyl)amino]carbonyl}carboxamide;
2H,3H-benzo[e]1,4-dioxan-6-yl-N-{[(3-(2-furyl)phenyl)amino]carbonyl}carboxamide;
2H,3H-benzo[e]1,4-dioxan-6-yl-N-{[(3-(2-pyridyl)phenyl)amino]carbonyl}carboxamide;
2H,3H-benzo[e]1,4-dioxan-6-yl-N-{[(4-(1H-1,2,3,4-tetrazol-5-yl)phenyl)amino]carbonyl}carboxamide;
methyl 5-{[(2H,3H-benzo[e]1,4-dioxan-6-ylcarbonylamino)carbonyl]amino}-2bromobenzoate;
3-{[(2H,3H-benzo[e]1,4-dioxan-6-ylcarbonylamino)carbonyl]amino}-5-(trifluoromethyl)benzoic acid;
2H,3H-benzo[e]1,4-dioxan-6-yl-N-({[3-hydroxy-5-(trifluoromethyl)phenyl]amino}carbonyl)-carboxamide;
5-{[(2H,3H-benzo[e]1,4-dioxan-6-ylcarbonylamino)carbonyl]amino}-2-bromobenzoic acid;
4-{[(2H,3H-benzo[e]1,4-dioxan-6-ylcarbonylamino)carbonyl]amino}-2-chlorophenyl acetate;
4-{[(2H,3H-benzo[e]1,4-dioxan-6-ylcarbonylamino)carbonyl]amino}-2-chlorophenyl methyl propane-1,3-dioate;
2-[(4-{[(2H,3H-benzo[e]1,4-dioxan-6-ylcarbonylamino)carbonyl]amino}-2-chlorophenyl)oxycarbonyl]-acetic acid;
methyl 2-(4-{[(2H,3H-benzo[e]1,4-dioxan-6-ylcarbonylamino)carbonyl]amino}-2-chlorophenoxy)-acetate;
2-(4-{[(2H,3H-benzo[e]1,4-dioxan-6-ylcarbonylamino)carbonyl]amino}-2-chlorophenoxy)acetic acid;
phenylmethyl 2-(4-{[(2H,3H-benzo[e]1,4-dioxan-6-ylcarbonylamino)carbonyl]amino}-2-chlorophenoxy)acetate;
4-{[(2H,3H-benzo[e]1,4-dioxan-6-ylcarbonylamino)carbonyl]amino}-2-chlorobenzoic acid;
5-{[(2H,3H-benzo[3,4-e]1,4-dioxin-6-ylcarbonylamino)carbonyl]amino}-2-chlorobenzoic acid;
4-{[(2H,3H-benzo[3,4-e]1,4-dioxin-6-ylcarbonylamino)carbonyl]amino}benzoic acid;
3-{[(2H,3H-benzo[3,4-e]1,4-dioxin-6-ylcarbonylamino)carbonyl]amino}benzoic acid;
2H,3H-benzo[3,4-e]1,4-dioxin-6-yl-N-{[(2-chloro(4-pyridyl)amino]carbonyl}carboxamide;
2H,3H-benzo[3,4-e]1,4-dioxin-6-yl-N-{[(6-chloro-4-methylpyrimidin-2-yl)amino]carbonyl}carboxamide;
2H,3H-benzo[3,4-e]1,4-dioxin-6-yl-N-({[5-(trifluoromethyl)(1,3,4-thiadiazol-2-yl)]amino}carbonyl)-carboxamide;
2H,3H-benzo[3,4-e]1,4-dioxin-6-yl-N-{[(3-chlorophenyl)(methoxymethyl)amino]carbonyl}-N-(methoxymethyl)carboxamide; and
2H,3H-benzo[3,4-e]1,4-dioxan-6-yl-N-{[(3-chlorophenyl)amino]carbonyl}-N-[(2-methoxy-ethoxy)methyl]carboxamide;
and the pharmaceutically acceptable salts thereof, as single stereoisomers or mixtures of stereoisomers.

26. A pharmaceutical composition comprising:
(a) a therapeutically effective amount of a compound of claim 1; and
(b) a pharmaceutically acceptable excipient.

27. The pharmaceutical composition of claim 26 further comprising an anti-inflammatory drug, cytokine, or immunomodulator.

28. A method of treating an allergic, inflammatory, or autoimmune disease in a mammal, comprising administration to the mammal of a therapeutically effective amount of a compound of claim 1.

29. The method of claim 28, where the disease is asthma.

30. The method of claim 28, where the disease is pulmonary fibrosis.

31. The method of claim 28, where the disease is diabetic nephropathy.

32. The method of claim 28, where the disease is rheumatoid arthritis.

33. The method of claim 28, where the disease is restenosis.

34. The method of claim 28, where the disease is pancreatitis.

35. The method of claim 28, where the disease is glomerulonephritis.

36. The method of claim 28, where the disease is atherosclerosis.

37. The method of claim 28, where the disease is inflammatory bowel disease.

38. The method of claim 28, where the disease is Crohn's disease.

39. The method of claim 28, where the disease is transplant rejection.

40. The method of claim 28, where the disease is associated with lymphocyte and/or monocyte accumulation.

\* \* \* \* \*